US007596541B2

(12) United States Patent
deVries et al.

(10) Patent No.: US 7,596,541 B2
(45) Date of Patent: Sep. 29, 2009

(54) METHOD AND APPARATUS OF ASSURING INFORMED CONSENT WHILE CONDUCTING SECURE CLINICAL TRIALS

(75) Inventors: Glen M. deVries, New York, NY (US); Edward F. Ikeguchi, Larchmont, NY (US); Alexis E. Te, Manhasset, NY (US)

(73) Assignee: Medidata Solutions, Inc., New York, NY (US)

(*) Notice: Subject to any disclaimer, the term of this patent is extended or adjusted under 35 U.S.C. 154(b) by 418 days.

(21) Appl. No.: 10/416,380

(22) PCT Filed: Nov. 13, 2001

(86) PCT No.: PCT/US01/51091

§ 371 (c)(1),
(2), (4) Date: May 9, 2003

(87) PCT Pub. No.: WO02/44868

PCT Pub. Date: Jun. 6, 2002

(65) Prior Publication Data

US 2004/0006553 A1  Jan. 8, 2004

(51) Int. Cl.
*G06F 7/00* (2006.01)
(52) U.S. Cl. .......................... 707/1; 434/234; 434/236; 432/262
(58) Field of Classification Search .................. 707/1, 707/5; 705/2; 434/234, 236, 323, 350; 432/262
See application file for complete search history.

(56) References Cited

U.S. PATENT DOCUMENTS

| 5,666,490 | A | | 9/1997 | Gillings et al. |
| 5,799,282 | A | * | 8/1998 | Rakshit et al. ................. 705/2 |
| 6,108,635 | A | * | 8/2000 | Herren et al. ................. 705/2 |
| 6,171,112 | B1 | * | 1/2001 | Clark et al. ................. 434/322 |
| 6,188,988 | B1 | * | 2/2001 | Barry et al. ................... 705/3 |
| 2001/0032210 | A1 | * | 10/2001 | Frank et al. .............. 707/104.1 |
| 2001/0034023 | A1 | | 10/2001 | Stanton, Jr. et al. |

OTHER PUBLICATIONS

Clinical Trials.Gov, U.S. National Library of Medicine, "An Introduction to Clinical Trials", Apr. 8, 2000, pp. 1-13.*

* cited by examiner

*Primary Examiner*—Sathyanarayan Pannala
(74) *Attorney, Agent, or Firm*—Fulbright & Jaworski LLP

(57) ABSTRACT

The present invention is a method for conducting clinical trials. The clinical trial consists of the inventive system (10); a computing device (12); application database (11*a*), the personnel database (11*b*), and the trial data database; computing devices (14*a*), (14*b*), and (14*c*) for use by trial participants and trial investigators; computing device (15); computer devices (16*a*), (16*b*), and (16*c*) for use by trial monitors; computing devices (18*a*), (18*b*), and (18*c*) for use by laboratories to connect via the network (20).

32 Claims, 18 Drawing Sheets

Blood Chemistry (If necessary at 3, 6, 12)

1. White Blood Cell Count — ((10)^3/ul)
2. Hemoglobin — g/dl
3. Platelets — ((10)^3/ul)
4. Serum Sodium — mmol/L
5. Serum Potassium — mmol/L
6. Serum Chloride — mmol/L
7. Serum Bicarbonate — mEq/L
8. Blood Urea Nitrogen — mg/dl
9. Hematocrit — %
10. Serum Creatine — mg/dl
11. Serum Glucose — mg/dl
12. Uric Acid — mg/dl
13. Calcium — mg/dl
14. Serum Phosphorous — mg/dl
15. ALT (SGPT) — U/L
16. Alkaline Phosphatase — U/L
17. Total Bilirubin — mg/dl
18. Total Serum Protein — g/dl
19. Serum Albumin — g/dl
20. Serum Cholesterol — mg/dl Submit Data

FIG. 4e

Sexual function questionnaire

1. Over the past 4 weeks, how often were you able to get an erection during sexual activity?
   No sexual activity
2. Over the past 4 weeks, when you had erection with sexual stimulation, how often were your erections hard enough for penetration?
   No sexual activity
3. Over the past 4 weeks, when you attempted sexual intercourse, how often were you able to penetrate (enter) your partner?
   Did not attempt intercourse
4. Over the past 4 weeks, during sexual intercourse, how often were you able to maintain an erection after you had penetrated (entered) your partner?
   Did not attempt intercourse
5. Over the past 4 weeks, during sexual intercourse, how difficult was it to maintain your erection to completion of intercourse?
   Did not attempt intercourse
6. Over the past 4 weeks, how many times have you attempted sexual intercourse?
   No attempts
7. Over the past 4 weeks, when you attempted sexual intercourse how often was it satisfactory to you?
   Did not attempt intercourse
8. Over the past 4 weeks, how much have you enjoyed sexual intercourse?
   No intercourse
9. Over the past 4 weeks, when you had sexual stimulation or intercourse how often did you ejaculate?
   No sexual stimulation or intercourse
10. Over the past 4 weeks, when you had sexual stimulation or intercourse how often did you have the feeling of orgasm or climax (with or without ejaculation)?
    No sexual stimulation or intercourse
11. Over the past 4 weeks, how often have you felt sexual desire?
    Almost never or never
12. Over the past 4 weeks, how would you rate your sexual desire?
    Very low
13. Over the past 4 weeks, how satisfied have you been with your overall sex life?
    Very dissatisfied

FIG. 4f

1. SAMPLE INFORMED CONSENT

CONSENT FOR PARTICIPATION IN A CLINICAL STUDY OF DISEASE X

Consent for Subjects

STUDY PURPOSE

You are invited to participate in a research study of patients with disease X. The purpose of this study is to evaluate methods of determining an individual's risk of having serious health problems. These methods involve analysis of tests performed upon the subjects. We will study the analysis of theses tests.

STUDY PROCEDURES

If you agree to participate in this study, you will have your tests measured at rest and during exercise. These two tests will be scheduled at your convenience.

STUDY RISKS

The risks of this study are minimal. Obtaining the tests involves no significant risk. In extremely rare circumstances these tests could lead to pain and a headache.

STUDY BENEFITS

No direct benefits to you are anticipated. Your participation in the study will be of benefit for the future treatment of disease X in that it may lead to the development of non-invasive methods of determining an individual's risk of serious problems.

FIG. 8a

ALTERNATIVES

The alternative to participating in this study would be to continue with your current treatment program, without having the additional tests performed.

COST AND COMPENSATION

You will only be charged for your regularly scheduled clinical care. You will not be charged any additional amount for the additional procedures involved in this research protocol. You will not receive any compensation for participating in this study.

CONFIDENTIALITY

Any information obtained during this study will remain confidential. I understand that my rights to privacy will be maintained. All information obtained on me during the course of the study will be kept confidential and accessible only to the Principal Investigator and his assistants. In publications of this research, I will not be identified by name.

PARTICIPATION IS VOLUNTARY

Your participation in the research study is completely voluntary. You can refuse to participate or withdraw from the study at any time and such a decision will not affect your medical care now or in the future. Signing this form does not waive any of your legal rights.

QUESTIONS

If you have any questions, please ask, and we will do our best to answer them. If you have additional questions in the future, you can reach Dr. Doe at 212-123-4567. If you have any questions about your rights as a research subject, you may contact the Institutional Review Board at 212-111-1111.

FIG. 8b

STATEMENT OF CONSENT

I have discussed this study with Dr. Doe to my satisfaction. I understand that my participation is voluntary and that I can withdraw from the study any time without prejudice. I have read the above and agree to enter in this research study. Signing this consent form does not waive any of my legal rights.

I have been informed that if I believe I have sustained injury as a result of participating in a research study, I may contact the Principal Investigator, Dr. Doe, at 212-123-4567, or the Institutional Review Board at 212-111-1111, so that I can review the matter and identify the medical resources that may be available to me.

I understand that:

The Hospital will furnish the medical care deemed necessary by the staff of this hospital.

I will be responsible for the cost of such care, either personally or through my medical insurance or other forms of medical coverage.

No monetary compensation for wages lost as a result of injury will be paid to me by The Hospital.

I will receive a copy of this consent form.

Patient's Signature _____ Date _____

Investigator's Signature _____ Date _____

FIG. 8c

| | | |
|---|---|---|
| Informed Consent | Please confirm that the patient has read, understands, and has signed an Informed Consent form.: 1 Informed Consent form is on file. | 02/06/2000 14:52 260726 |
| Informed Consent | Please confirm that the patient has read, understands, and has signed an Informed Consent form.: 1 Informed Consent form is on file. | 02/06/2000 14:53 677987 |
| Informed Consent | Please confirm that the patient has read, understands, and has signed an Informed Consent form.: 1 Informed Consent form is on file. | 02/06/2000 14:52 202660 |
| Informed Consent | Please confirm that the patient has read, understands, and has signed an Informed Consent form.: 1 Informed Consent form is on file. | 02/06/2000 14:53 591937 |
| Informed Consent | Please confirm that the patient has read, understands, and has signed an Informed Consent form.: 1 Informed Consent form is on file. | 02/06/2000 14:53 544228 |
| Informed Consent | Please confirm that the patient has read, understands, and has signed an Informed Consent form.: 1 Informed Consent form is on file. | 02/06/2000 14:53 435165 |
| Informed Consent | Please confirm that the patient has read, understands, and has signed an Informed Consent form.: 1 Informed Consent form is on file. | 02/06/2000 14:53 664968 |
| Informed Consent | Please confirm that the patient has read, understands, and has signed an Informed Consent form.: 1 Informed Consent form is on file. | 02/06/2000 14:53 103365 |
| Informed Consent | Please confirm that the patient has read, understands, and has signed an Informed Consent form.: 1 Informed Consent form is on file. | 02/06/2000 14:53 167072 |

FIG. 8d

METHOD AND APPARATUS OF ASSURING INFORMED CONSENT WHILE CONDUCTING SECURE CLINICAL TRIALS

FIELD OF THE INVENTION

This invention relates to authenticating that a recorded event occurred in a proscribed manner and was performed by authorized personnel. More specifically, this invention relates to assuring that the recorded event occurred with an informed consent.

BACKGROUND OF THE INVENTION

Companies in the pharmaceutical and biotechnology industries annually funnel huge monetary investments into research and development (R&D) of new medical technology, i.e., drugs, medical devices, and new methods or techniques to diagnose and treat medical disorders. The life cycle of any new medical technology generally originates in a laboratory, after which the new medical technology undergoes several phases of investigation to prove its safety and efficacy. Once a sufficient body of evidence has been amassed to assure such safety and efficacy, the new medical technology is sent before a regulatory committee for review. If the medical technology is subsequently approved, it can then be marketed for sale and sold, enabling the companies investing in that new medical technology to begin to realize the return on their investment in the development of the new technology. The life cycle for most of the new medical technology is lengthy; for example, as of 1997 the process of developing a new medical technology from laboratory to marketing took an average of 10 to 12 years.

Over the past decade a new industry has arisen as an adjunct to the clinical research process of developing new medical technologies. R&D service providing organizations, known as Contract Research Organizations (CROs) arose out of a growing need among the pharmaceutical and biotechnology companies to curb costs. Rather than hiring full-time research staff, companies turned to CROs as a resource for these companies to outsource the administrative and coordinating responsibilities for clinical research. Over time CROs compounded other value-added services to encompass a spectrum of services, including clinical trial coordination, monitoring of data collection, identification of quality research trial investigators and sites, and centralized laboratory testing. The development of the CROs was also logical for other reasons, including the favorable implications for the pharmaceutical and biotechnology companies to have their new medical technology tested under the unbiased eye of a third-party organization.

One of the greatest claims made by the CROs is the ability of their trained staff professionals to shorten the amount of time required to complete a research project, which would in turn shorten the amount of time required to pass regulatory scrutiny. As can be recognized from the protracted 10 to 12 year development period described above, such shortening of the life cycle time is very desirable for most pharmaceutical and biotechnology companies. This is especially true because while a newly invented drug or medical device may be patented upon discovery, with the 20 year patent term commencing on the date of filing of the patent application, such new medical technology does not become profitable until it is approved, marketed, and sold. Thus, if as described above, it can take 10 to 12 years for the new technology to become profitable, there will only be a limited portion of the patent term remaining.

It is not inconceivable that after spending millions on R&D and after facing a tough regulatory approval process, a pharmaceutical or biotechnology company would have but 2 to 5 years of exclusivity to exploit the exclusion sale of the new medical technology. Such outcome is ultimately detrimental: it discourages R&D in the medical field, encourages hasty clinical research to expedite the regulatory process, and places smaller to mid-sized companies at a distinct disadvantage to the established "health care giants." The protracted pre-marketing time, particularly in the United States, has also been criticized as being a barrier to the passage of vital new medical technologies. In many cases, life-saving drugs can only be obtained in settings of research or in markets outside the control of the United States government.

Despite the emergence of the CROs, their services are still severely under utilized. It is estimated that in the United States less then 20% of the medical R&D market is captured by the CROs. These figures are far smaller outside of the United States, particularly in Europe and Japan.

Life Cycle

Typically, a clinical trial is carried out in the following manner: At the initiation of a clinical trial, the company sponsoring the trial or the CRO contracted for the trial (the "sponsor") will select a number of trial investigators. These trial investigators are usually doctors who specialize in the area of medicine relevant to the new medical technology under study. The trial investigators are chosen based upon several criteria, including:

1) The number of trial participants seen and the ability of the trial investigator to accrue trial participants into the study.
2) The facility and support staff available to the trial investigator.
3) The trial investigator's ability to collect and maintain data in a secure fashion without compromising trial participant confidentiality or care.

A trial protocol will be formulated to achieve the desired goals of the trial, and the protocol will be presented for review and approval before an Institutional Review Board (IRB). The IRB is a committee consisting of peers and people with experience in the research field. It may consist of physicians, nurses, PhD's, bio-statisticians, bio-ethicists, and/or others qualified to evaluate research on human. The IRB evaluates research protocols to assure scientific integrity while maintaining the trial participants' safety and privacy within a standard of ethics acceptable for human experimentation. Once a clinical trial is under way, the trial investigators do the following:

1) Begin recruiting trial participants that fit the inclusion/exclusion criteria of the protocol.
2) Explain the risks and benefits of the trial to the trial participants.
3) Ask the trial participants to give an informed consent.
4) Apply new medical technology, i.e., administer medical treatments.
5) Initiate and continue trial data collection.

The trial data is collected by the trial investigators in the form of reports that are then forwarded to the sponsor. Reporting generally takes the form of paper sheets that are handwritten and transmitted via fax or placed into digital form with the use of an electronic scanner. These reports generally serve as the data collection vehicle with various parameters studied as outlined in the particular protocol. The parameters studied in a clinical trial may include subjective findings such as trial participants' complaints, satisfaction, or symptoms. Objective parameters may also be studied, which parameters include physical examination, laboratory or radiological tests, and other measured findings. Finally, a separate parameter followed in almost all trials is incidence of adverse events or complications from the treatment.

In the course of a clinical trial, an important responsibility is that of a trial monitor. The trial monitor is a person who is usually hired by a CRO to verify that the data reported by the trial investigators corresponds to the source documentation, i.e., the trial participants' clinic records. The trial monitor serves as an auditor of the trial investigators to police the integrity of the data collected. The trial monitor also assures that all documentation, such as each trial participant's informed consent, is properly signed and that the trial investigators stay true to the procedure set forth in the trial protocol. The trial monitor also checks to assure that the reports forwarded to the sponsor correspond to the actual medical records documented by a trial investigator in a trial participant's chart.

As the clinical trial progresses, the sponsor is made cognizant of the overall status of the trial. For example, if an inordinate number of complications arise from the medical treatment, it is the sponsor's responsibility to know of the problem and to react. Sometimes such reactions may prematurely halt the trial. Conversely, it is not uncommon for the new medical technology to be so effective that the reaction and the responsibility of the sponsor is to offer the new medical technology to more trial participants.

At the end of the trial, a stage of trial "closing" is conducted. During this stage all reports are finalized and any missing data is reconciled by the trial investigators. After this, the sponsor consolidates the data collected during the trial for statistical analysis. The results of such analysis are then made available for reporting to the regulatory bodies and/or academic publishing.

Detriments

There are many instances where the life cycle described above falls short of its optimal potential. In fact, negative reports and issues of the shortcomings of medical R&D are in the news daily. In January 2000, all human gene therapy experiments carried out at an Ivy League university and sponsored by the United States government was halted after the death of a trial participant. After further review, there was evidence that the trial participant was not provided proper informed consent. In addition to simple human error, there are ample situations where monetary pressure may lead to potential fraud by the trial investigator and/or the sponsor. Such fraud may include the falsification of the trial data, loose interpretation of the trial protocols to allow into a study trial participants who may not be proper candidates, statistical manipulation to allow results to appear better than actual, under-reporting of adverse events, etc. There have even been situations where an entire group of trial participants reported upon in the trial, did not even exist.

In the early 1990's the National Surgical Adjuvant Breast and Bowel Project ran a clinical trial evaluating benefits of performing mastectomy for trial participants with breast cancer versus lumpectomy with or without radiation. During this trial, one of the site directors, the equivalent of the trial investigator, falsified the dates of certain events of the trial, in order to allow ineligible trial participants to appear eligible for the research. This ultimately resulted in a massive government investigation costing millions of dollars, a delay in the availability of the trial results affecting thousands of patients with breast cancer, skepticism concerning the trial results, loss of the trial investigator credibility, and the derailment of the careers of several prominent academic figures.

The potential for similar situations to recur forces the increased stringency of regulatory processes, thus adding to the already long life cycle period required before marketing and sale of the new medical technology.

Consent

It should be noted that in the life cycle of performing clinical research, the solicitation of the proper informed consent from the patient is a critical part of meeting ethical and legal standards. Informed consent is a major area of fraud and error during the clinical research process. These errors and instances of fraud relate to several major areas which include episodes where:

1) The research investigator (typically the doctor responsible for the trial) does not explain the content of the informed consent document for which the patient's signature is solicited;
2) The occurrence of informed consent is backdated;
3) The patient's or investigator's signature is forged on the informed consent.

Recently the U.S. government has initiated steps to assure better patient safety for enrollees in clinical research projects. At the forefront of this initiative is the implementation of strict guidelines for the execution of informed consents. These guidelines would include intervals during the clinical trial for which the informed consent would be required, or triggering events during the clinical trial process that might alter the implications of trial enrollment for the patient, i.e., the occurrence of adverse events. Additionally, the government will enforce serious penalties for failures to obtain the proper informed consent, including fines of $250,000 per individual and $1 million per institution.

In another governmental initiative the Food and Drug Administration (FDA) laid out guidelines that clearly define the manner in which electronic records can be signed using at least two distinct tokens, such as a user name and password 21 C.F.R. § 11.200(1) (2000). The prerequisite to the use of an electronic signature, however, is that the organization assigning the electronic signature has verified the identity of the individual 21 C.F.R. § 11.100.(b) (2000).

With the proliferation of electronic data collection in clinical research there is and will continue to be an exponentially increasing need for the use of electronic signatures. This increase makes the collection of physical signatures and verification processes unrealistic, especially in cases where geographically broad populations of users must be quickly granted access to a particular system Evolution In view of the pressures placed upon the sponsors in terms of time expenditure while sustaining the scientific rigor, several CROs and industry specialists have begun implementing digital formats for data collection. Digital data collection and collaboration of research over digital networks have the potential for multiple advantages. These advantages include the ability to consolidate the trial data into a single database as the trial data is being collected, thus allowing for the analysis of data in real time. In addition, data can be validated upon entry, ultimately resulting in less time spent at the end of the trial to reconcile "loose ends" in the data collection process. These and other advantages of electronic data collection are clearly superior to conventional methods of handwritten forms, scanning, and faxing. However, many concerns still exist over issues of data security, trial participant privacy, and veracity of the collected data.

Furthermore, while electronic data collection has the potential to improve upon the time expenditure in the clinical trial process, it does not resolve the need to vigorously monitor the trial for fraud. In other words, while the electronic data collection makes the clinical trial process faster, it does not improve the scientific rigor with which the trial investigators collect and report upon the trial data.

In any clinical research setting the key event leading to the generation of data is that between two individuals: the trial participant, e.g., a patient, and the trial investigator, e.g., a doctor. In conventional methods, this interaction is the event that is documented in the trial participant's medical records and is a reflection of the trial participant's physical examination, reports of subjective complaints, interpretations of objective testing, and a synthesized analysis of the trial participant's information as a function of the trial investigator's professional training.

The conventional methods of clinical research rely upon a trial investigator's signature on a paper document. This creates ample of opportunity for fraud and an obvious need for strict monitoring. As the clinical research field looks more to digital data capture and transmission, there is a greater need to authenticate the information. While various methods have been proposed for digital authentication of individuals, what is needed is the authentication that a recorded event occurred in a proscribed manner and was performed by authorized personnel. This event may include the interaction between two or more authorized personnel, such as the doctor and patient. Moreover, such authentication must lead to the acceptance or rejection of the trial data in a clinical study or trial.

SUMMARY OF THE INVENTION

The present invention is a method of conducting clinical trials. Each clinical trial includes members comprising trial administrators, trial monitors, trial investigators, and trial participants or patients. Additionally, these members may include reporters, scientists, and others interested in sampling the results of the study as it progresses. The trial administrator selects the trial monitors, persons responsible with assuring the veracity of the study, and the trial investigators, persons such as nurses and doctors who will actually administer the study or trial. The trial administrator will further define procedural guidelines for the performance of the clinical trial. The trial investigators in turn will select the trial participants or patients to be enrolled in the clinical trial. The trial monitors observe the conduct of the clinical trials to detect any deviations from the procedural guidelines previously established by the trial administrator.

The present invention allows the clinical trial to be conducted over a network, e.g., the Internet or a telephone grid. The participants use computing devices connected to the network to perform transactions of the clinical trial. Each of the tests comprises one or more periods of execution or intervals, test elements, and a plurality of exception limits. All the trial participants are listed in a database and are assigned access and validation levels. The clinical trial is performed according to the procedural guidelines by carrying out all of the transactions of the clinical trial. The executed transactions are stored in a database. Any time during the performance of the clinical trial the stored transactions can be queried at random to assure veracity of the clinical trial and to notify the trial administrator if any discrepancy is found to prevent fraud.

Each transaction of the inventive method is performed by one of the members initiating a session by establishing a data path from a computing device equipped with various authentication hardware and/or software, to the computing device on which the inventive method is implemented. As the connection is established and the member has logged in, the invention determines what level of access is allowed and what level of authentication is required for the logged-in member. After performing the required authentication method, the members who are the trial participants and the trial investigators are shown a plurality of tests to choose from. When the required test is selected, the trial data entry may begin.

The trial participants and the trial investigators are asked to reply to a plurality of questions or enter information corresponding to various elements of the test. Each of the entered values is immediately evaluated to determine if values entered are outside of the exception limits. The exception limits may be default or custom set by the trial administrator. If the exception limits are exceeded, the trial participants and the trial investigators are asked to verify if the values are correct.

The login authentication process initiates or starts the clock running on a time range within which data entry or the current session must conclude in situations where the interaction of the members of the clinical trial is authenticated, the login authentication process may include the input of more than one authorized personnel or member of the clinical trial during the established time range. Regardless of the number of authenticated parties or members of the clinical trial, the data entry may occur as follows:

1) before the authentication of all necessary parties or members of the clinical trial;
2) sandwiched in between authentications, e.g., at least one authentication followed by data entry which is followed by at least one authentication or re-authentication, and so on; and/or
3) after the authentication of all necessary parties or members of the clinical trial.

Transactions failing that test may not be committed to the database, i.e., the results will be discarded.

After logging in, the members who are the trial monitors and the trial administrators may be allowed to execute various reports and queries on the information collected by the clinical trial up to date. Such reports and queries may assist these members in assuring that the clinical trial adheres to its procedural guidelines and therefore the data collected is beyond reproach.

BRIEF DESCRIPTION OF DRAWINGS

The foregoing objects and advantages of the present invention may be more readily understood by one skilled in the art with reference being had to the following detailed description of a preferred embodiment thereof, taken in conjunction with the accompanying drawings wherein like elements are designated by identical reference numerals throughout the several views, and in which:

FIGS. 4b-4f are a sample screen of the clinical trial management program listing various test and intervals at which these tests are to be performed.

FIGS. 8a-8c is a sample informed consent form.

FIG. 8d is a display of a log of informed consent use during the execution of the trial.

DETAILED DESCRIPTION OF THE INVENTION

Figure 1:
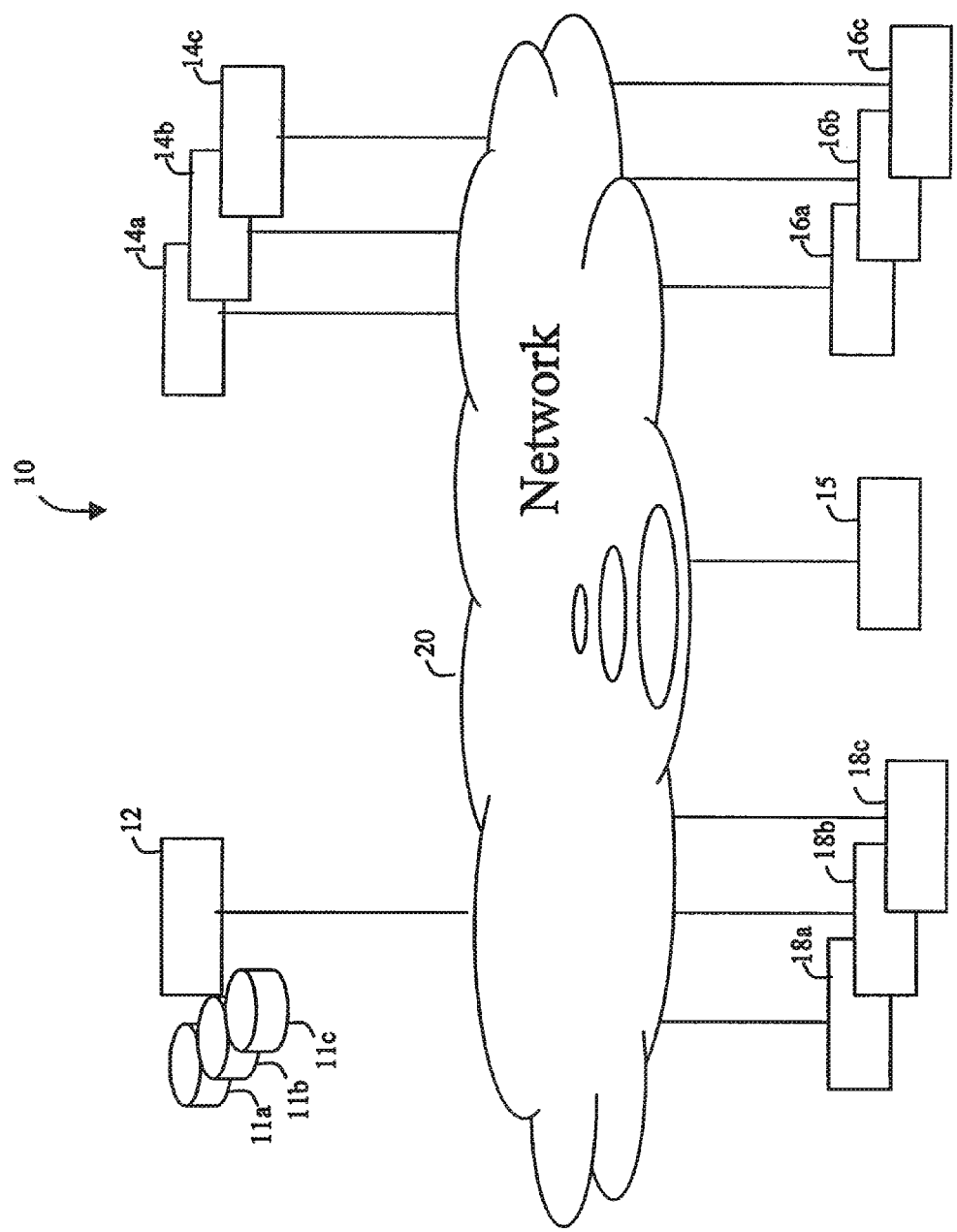
FIG. 1 is a network topology diagram, showing connectivity of various parts of the system of the present invention.

As shown in FIG. 1, the inventive system 10 comprises computing devices 14, i.e., 14a, 14b, 14c, for use by trial participants and trial investigators, computing devices 16, i.e., 16a, 16b, 16c, for use by trial monitors, a computing device 15 for use by a trial administrator, and computing devices 18, i.e., 18a, 18b, 18c, for use by laboratories to connect via the network 20 to a computing device 12, where the trial management program of the present invention is executed. Computing device 12 maintains and utilizes databases 11 which include an application database 11a for defining trials, i.e., scopes of studies, a personnel database 11b for defining persons authorized to access the inventive system residing on computing device 12, and a trial database 11c for saving and maintaining information collected with reference to the trials of the applications database 11a. The databases 11 do not have to be physically distinct, any distinction is made herein only for the purpose of clarity of description; in fact these databases 11 may be subdivided into more discreet units. Computing device 12 gathers the trial data submitted through computing devices 14 and 16 for the purpose of collecting that information in the trial's database 11c. The network 20 may be any type of a network, including a telephone network, a local area network, e.g., the Intranet, and a wide area network, e.g., the Internet.

Figure 2:
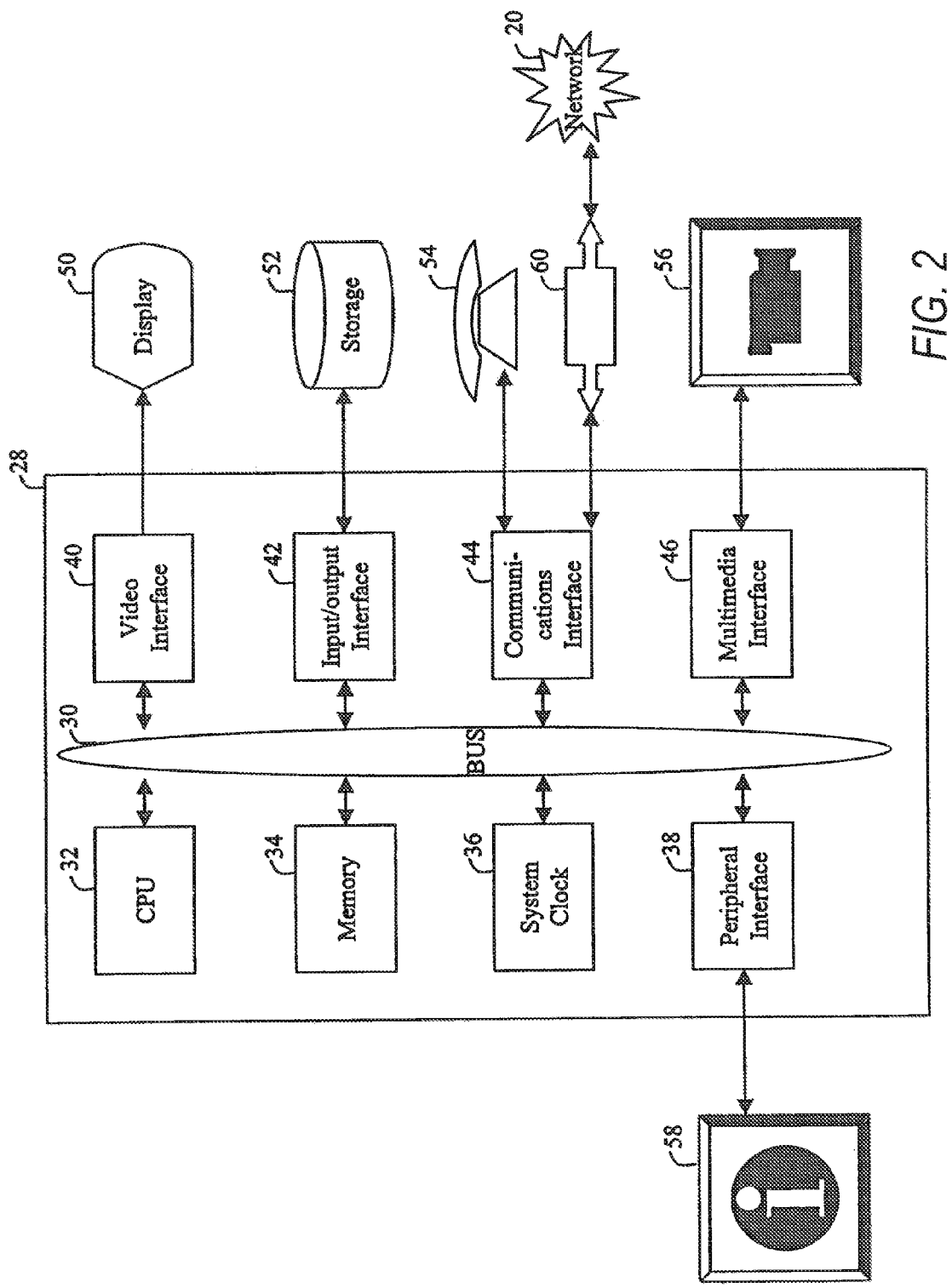
FIG. 2 is a diagram of the hardware components of computing devices used by the system of the present invention.

The computing devices 12, 14, 15, 16, and 18 may take the configuration of any computer ranging from mainframes and personal computers (PCs) to digital telephones and hand held devices, e.g., PALM PILOT™ personal assistance devices. In one illustrative embodiment of this invention shown in FIG. 2, such a computing device may comprise a bus 30, which is connected directly to each of the following: a central processing unit (CPU) 32; a memory 34; a system clock 36; a peripheral interface 38; a video interface 40; an input/output (I/O) interface 42; a communications interface 44; and a multimedia interface 46.

The common bus 30 is further connected by the video interface 40 to a display 50; by the I/O interface 42 to a storage device 52, which may illustratively take the form of memory gates, disks, diskettes, compact disks (CD), digital video disks (DVD), etc.; by the multimedia interface 46 to any multimedia component 56; by peripheral interface 38 to the peripherals 58, such as the keyboard, the mouse, navigational buttons, e.g., on a digital phone, a touch screen, and/or writing screen on fill size and hand held devices, e.g., a PALM PILOT device™; by the communications interface 44, e.g., a plurality of modems, to a network connection 60, e.g., an Internet Service Provider (ISP) and to other services, which is, or are, in turn connected to the network 20, whereby a data path is provided between the network 20 and the computing devices 12, 14, 15, 16, and 18 (FIG. 1) and, in particular, the common bus 30 of these computing devices: and furthermore, by the communications interface 44 to the wired and/or the wireless telephone system 54.

Defining Trial Data

Before clinical trials are carried out they are defined by values that may be placed into the application database 11a (FIG. 1). The entity, person, or persons creating, authoring, or instigating the trial driven by the inquiry into the hypothesis under study in a particular clinical trial is (or are) called the trial administrator. The trial administrator defines every aspect of any clinical trial, which may be administered by the inventive system.

Figure 3B:
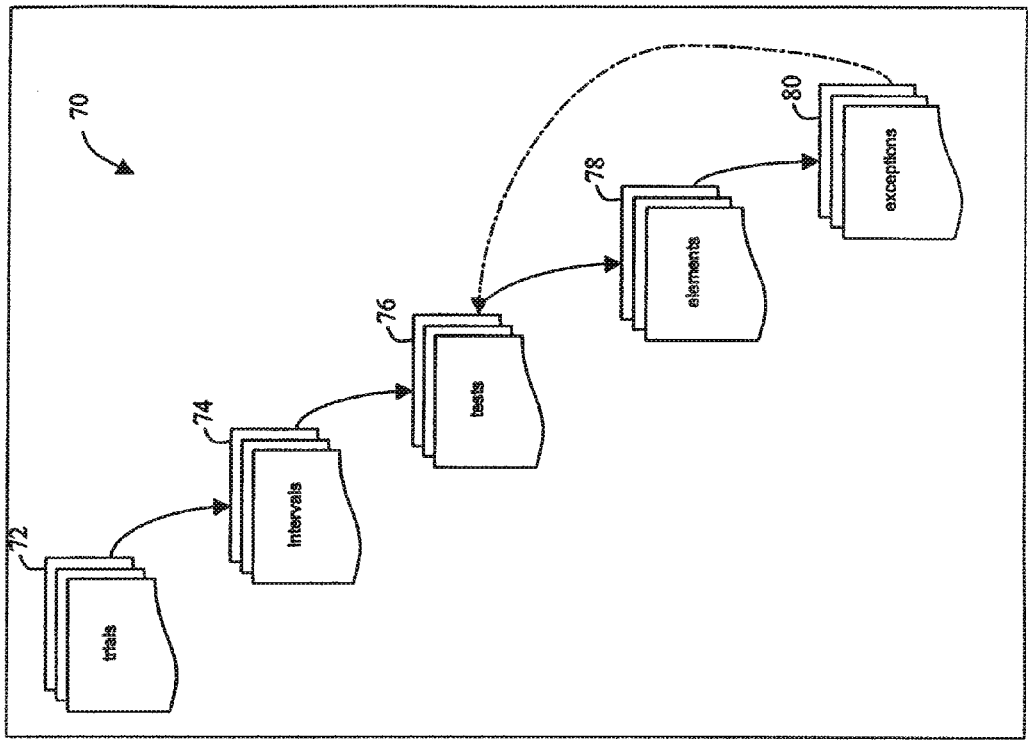
FIG. 3b is a logical relationship design diagram of elements comprising the records of the application database.

Each aspect of the clinical trial of the inventive system is defined by one of a series of database tables 70, shown in FIG. 3b. These tables 70 may be developed and managed with the help of any modem database management software, such as ORACLE, SYBASE, MICROSOFT ACCESS™, and others. After being defined, the tables 70 are stored in the application database 11a (FIG. 1). Each of these tables 70 references other tables 70 by the virtue of a relational architecture.

Figure 3A:
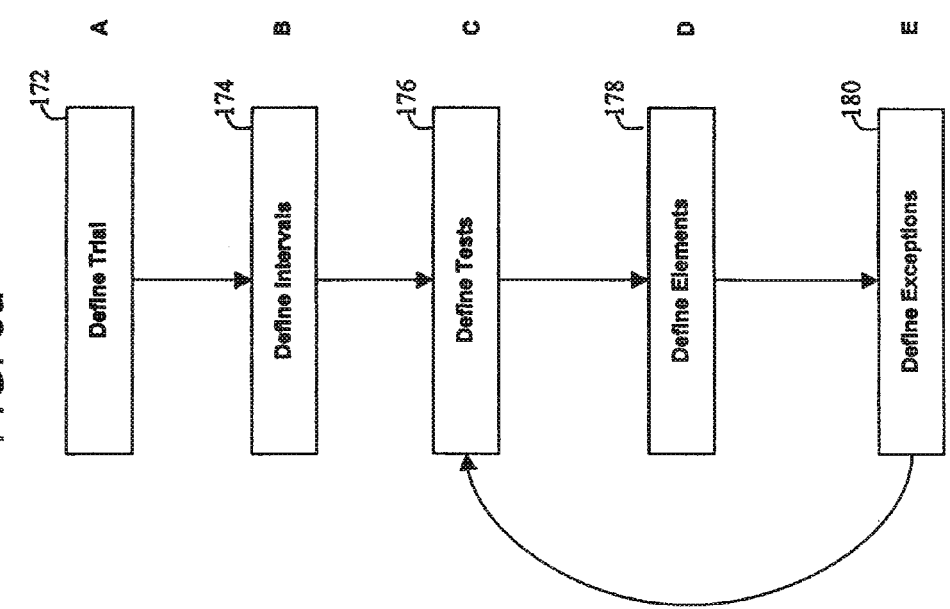
FIG. 3a is a flow diagram of a database entry program of the present invention, used to populate the application database.

The inventive system provides a method to enable the creation of the tables 70 to define the anticipated application data. The hierarchical sequence of the method is shown in FIG. 3a. There, in step 172, the table defining parts of a clinical trial 72 (FIG. 3b) is defined, including the structure of the trial, i.e., randomized, prospective, placebo-controlled, etc.; and the number of patients or trial participants to be enrolled in the trial.

Each of the records entered into the table 72 (FIG. 3b) would then be further defined in other related tables in the database 11a (FIG. 1). Thus, at step 174 the time intervals table 74 (FIG. 3b) comprises timing information regarding individual tests, which may be defined, for example:

1) the actual intervals of the study;
2) the margin of flexibility allowable in defining the time intervals; and
3) the test determinations made at each interval.

The tests table 76 (FIG. 3b), in turn, is defined in step 176 by listing the tests, e.g., the blood; the urine; the weight; and a quality of life questionnaire, to be performed and replied to. Elements of each test 76 may be further defined in step 178 in the elements table 78 (FIG. 3b), which may comprise test parameters such as:

1) test name;
2) upper and lower limits of normal;
3) informed consent requirement, i.e., in response to adverse event tests;
4) normal rates of change;
5) optional versus mandatory status of the test;
6) the type of data entry required, i.e., date, number, Boolean, text, etc.; and
7) the data entry vehicle used, i.e., checkbox, text field, a pointer to a data file such as a music format or a digital image, or an interfaced piece of hardware utilized to obtain data.

Each test element 78 (FIG. 3b) may be determined to have particular exceptions. Exceptions are values or data points entered outside the predefined protocol intervals and tests. They are implemented in order to handle data for patient complications or adverse events, or other points of planned or unplanned data entry. In other words, exceptions are a determination by the trial administrator of what is to be considered abnormal, e.g., body temperature below 96° or above 106° Fahrenheit. In step 180 exceptions 80 (FIG. 3b) will be defined for each data element 78 of each test 76 (FIG. 3*b*) calling for such exceptions. Not every element 78 or test 76 may require an exception.

The present application enables each part of one of the clinical trials in tables 72 (FIG. 3*b*) as defined by its elements in related tables 78 to be reusable, i.e., may be used to perform multiple clinical trials. In this manner, basic elements commonly found in clinical trials could be made available in a custom generated clinical trial. For example, the trial administrator trying to create a clinical trial may be presented with a panel of trial parts such as patient, doctor, blood test, heart exam, etc. Any trial element may be incorporated into a trial in a "drag-and-drop" or other fashion.

Figure 4A:
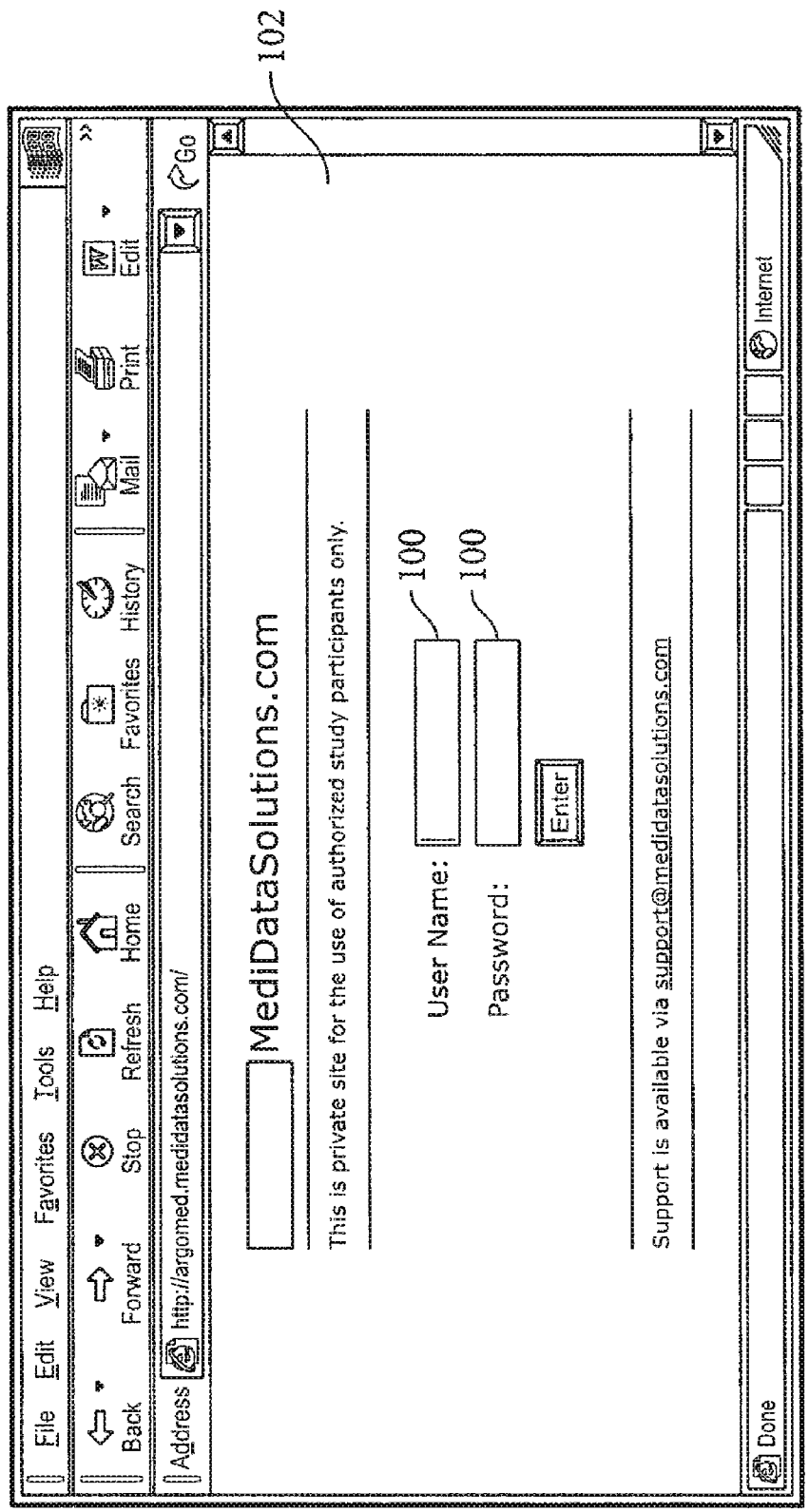
FIG. 4a is a sample login screen for gaining access to the clinical trial management program of the present invention.

The trial administrators desiring to create or design clinical trials may do so by establishing a data path from the computing device 15 (FIG. 1) to the computing device 12, via the network 20 to access the clinical trial management program of the present invention. This can be accomplished by using an Internet-based browser program, e.g., Microsoft EXPLORER™ or Netscape NAVIGATOR™. After connecting to the computing device 12 (FIG. 1), and entering the username/password combination 100, on the login screen 102 of the inventive system as shown in FIG. 4*a*, the trial administrator may create a new trial and begin defining the various elements of the trial. Furthermore, although after the start of the trial modifications may not be accepted, to create new trials the trial administrator may modify and delete any existing trials.

Figure 4B:
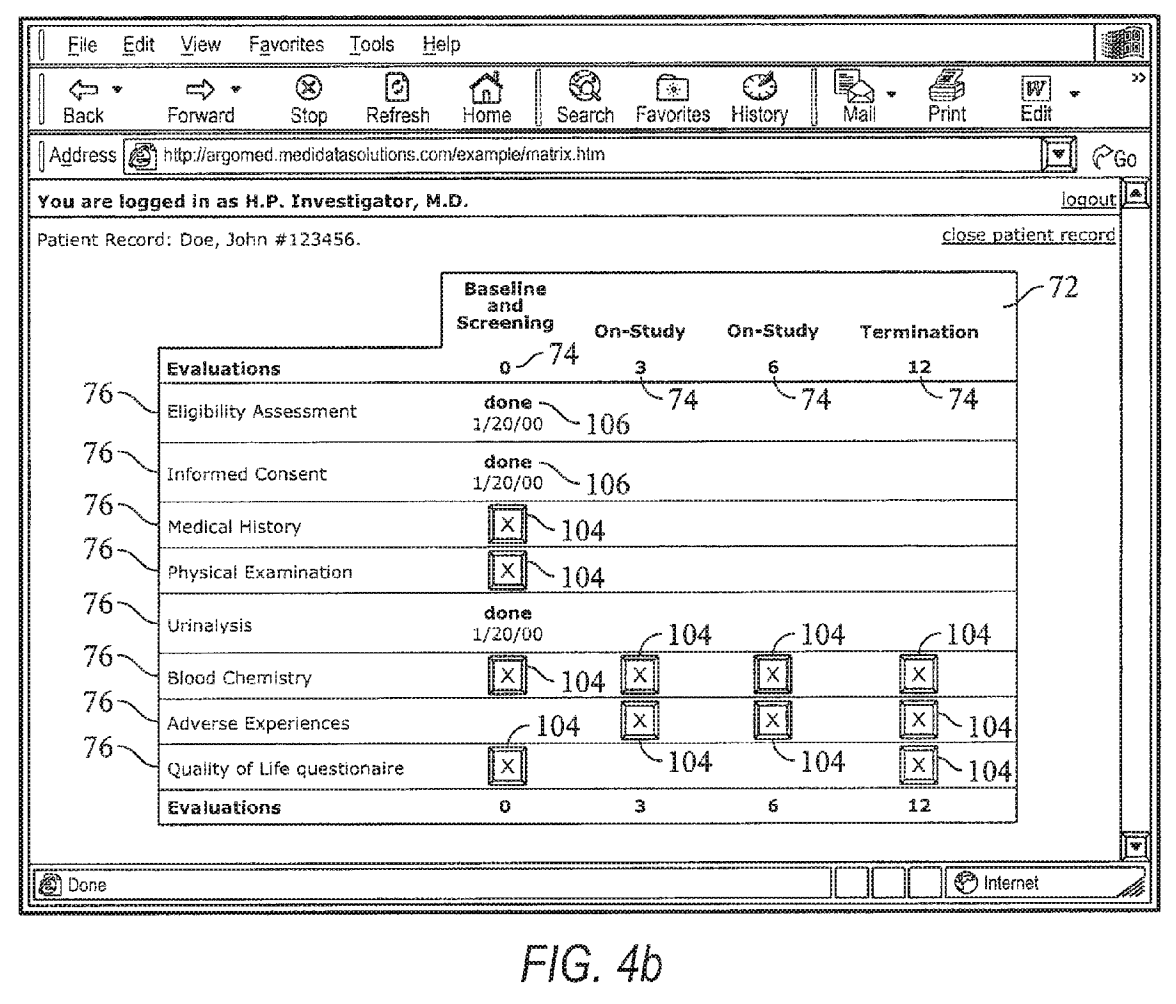
Figure 4C:
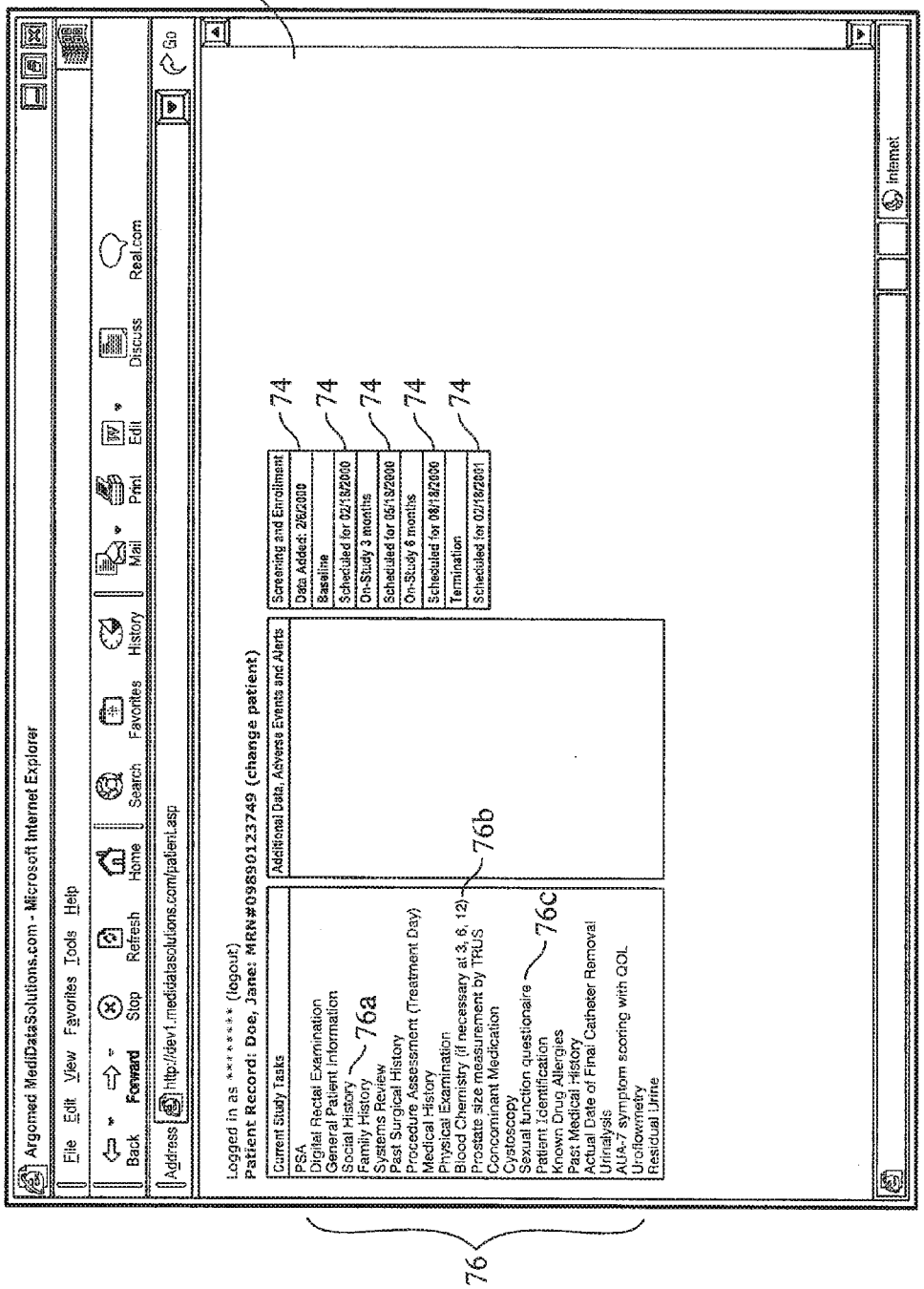

For example, FIGS. 4*b* and 4*c* show the clinical trial 72 comprising intervals 74 and tests 76. When screen buttons 104 are clicked, further components of the trial record 72, e.g., test elements 78 (FIG. 3*b*) and the exceptions 80 (FIG. 3*b*) may be displayed. Description "done" 106 indicates that the particular test 76 for the particular interval 74 has been performed.

Defining Personnel Data

As part of development of the clinical trial, the trial administrators will be able to establish or modify an existing list of trial investigators and trial monitors in the personnel database 11*b* (FIG. 1) for the particular trial being developed. Moreover, the trial investigators will be able to enter into the personnel database 11*b* (FIG. 1), lists of names of trial participants/patients selected to participate in the particular study after the trial is developed and is being carried out.

Each entry, i.e., a person's name and pertinent data, of the database 11*c* (FIG. 1) will have an associated set of pre-established permission standards, different permission standards for the trial participants, trial investigators, and trial monitors. These permission standards define the level of access available to each of the trial participants, trial investigators, and trial monitors involved in the trial to the application data in the database 11*a* (FIG. 1), the personnel data in the personnel database 11*b* (FIG. 1), and the trial data in the database 11*c* (FIG. 1). For example:

1) The trial participant/patient would have access to subjective questionnaires in the application data in the database 11*a* (FIG. 1) without access to any other data collected by the inventive system.
2) The trial investigator will have access to patient specific information in the database 11*c* (FIG. 1), by patient name and by patient number as well as to summary data within the scope of his or her own results. The trial administrator may also be able to define the type of investigator enrollment, e.g., an open enrollment allowing anyone qualified to act as the trial investigator to sign up or register as the trial investigator in the personnel database 11*b* (FIG. 1).

Alternatively, in an enrollment by invitation only, the trial administrator may choose to develop a trial whereby the trial investigators may have to make a telephone call, email, or mail correspondence to the trial administrator to request and to be furnished the login information. Before furnishing such login information, the trial administrator would update the entries of the personnel database 11*b* (FIG. 1) to give these invited trial investigators access to the inventive system. The receipt of the login information would enable the trial investigator to sign up in the trial investigator registration saved in the personnel database 11*b* (FIG. 1) on the computing device 12 (FIG. 1).

3) The trial monitor will have access to patient specific information saved in the trial data database 11*c* (FIG. 1) and identified by patient number, i.e., no patient names are revealed.
4) The trial administrator, in addition to full access to the application data database 11*c* (FIG. 1), will have access only to summary data of the trial database 11*c* (FIG. 1) for the entire trial without specific patient information.

Figure 7:
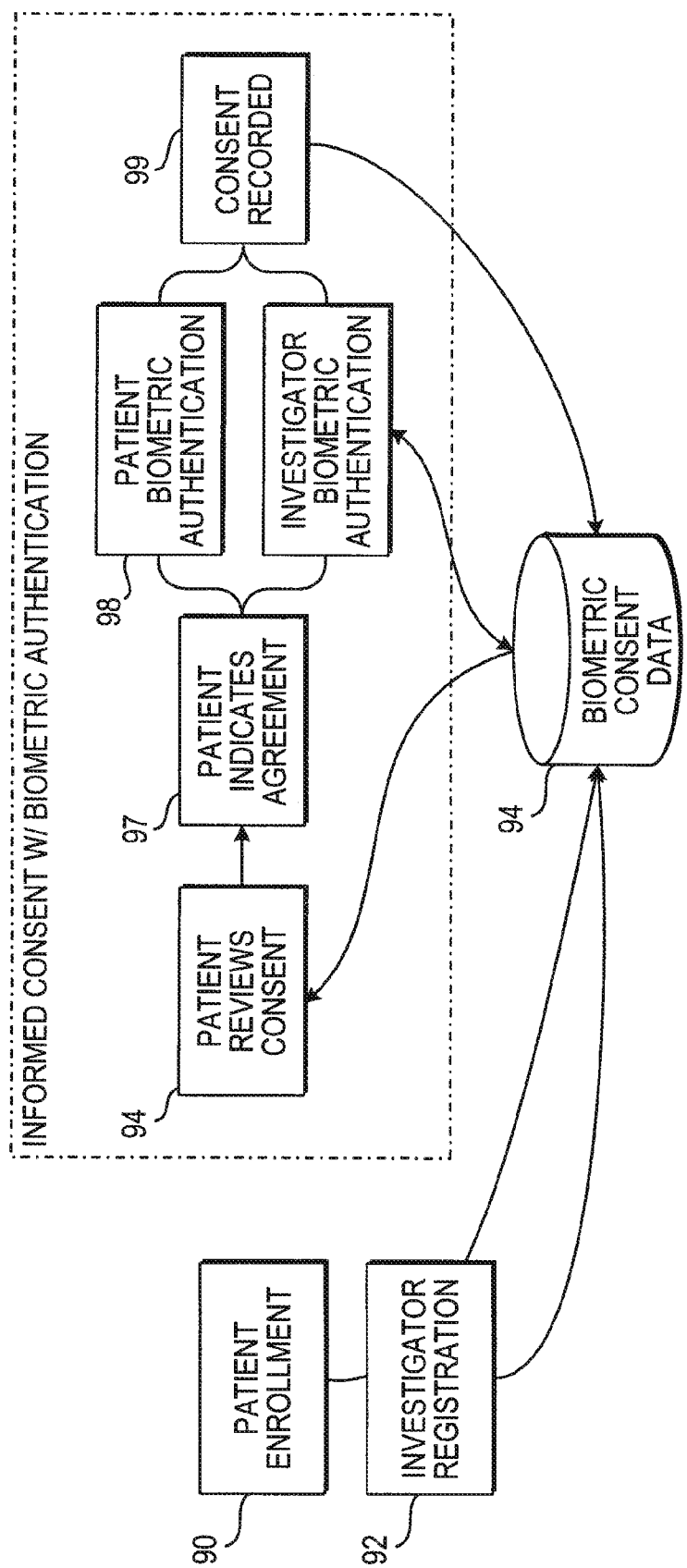
FIG. 7 is a flow diagram of the informed consent with biometric authentication.

Moreover, as shown in FIG. 7, all trial participants and all trial investigators are asked, in steps 90 and 92 respectively, to provide a baseline biometric reading, consisting of one or more of voiceprint, fingerprint, iris scan, electronic signature or other biometric modality, along with one or more identifiers such as their name, a user name and password combination, etc. The identifiers may be entered into text boxes on the computer screen. The provided biometric information and identifiers are then permanently recorded into the biometric consent database 94. This information may also be recorded, along with a database identifier that relates the patient's biometric record with other clinical research data, in another data repository or within the biometric consent database 94 itself.

This biometric consent database 94 will be used in step 95, during the performance of the trial, described in detail below, to obtain informed consent verified with biometric authentication from the enrolled trial participants and investigators. The informed consent may be requested at any time during the performance of the trial as dictated by the one or more clinical trials the trial participants are participating in, as well as any food and drug administration's rules regarding informed consent.

Performance of Trial

Once the particular trial has been completely defined or created in the application data database 11*a* (FIG. 1), the trial may commence. After the trial is activated, the parameters defining the trial in the database 11*a* (FIG. 1) can no longer be manipulated. To facilitate creation of new trials, the entire existing trial may be copied to create a new trial and that trial's parameters may be modified.

To run a trial, the trial administrator contracts the trial investigators to select the trial participants and begin patient enrollment and data collection regarding these trial participants. The trial administrator further contracts the trial monitors to monitor the veracity of the trial data. The trial participants are selected, and lists of names of the trial participants are entered into the personnel database 11*b* (FIG. 1). As shown in FIG. 7, in step 90 all trial participants, and in step 92 all trial investigators are asked to provide a baseline biometric reading, consisting of one or more of voiceprint, fingerprint, iris scan, electronic signature or other biometric modality, along with one or more identifiers such as their name, a user name, a password combination, etc. The identifiers may be entered into text boxes on the computer screen. The provided biometric information and identifiers are then permanently recorded into the biometric consent database 94. This information may also be recorded, along with a database identifier that relates the patient's biometric record with other clinical research data, in another data repository or within the biometric consent database 94 itself. This biometric consent database 94 will now be used in step 95 to obtain informed consent verified with biometric authentication from the enrolled trial participants and investigators. The informed consent may be requested at any time, as dictated by the one or more clinical trials the trial participants are participating in, as well as any food and drug administration's rules regarding informed consent.

Figure 5:
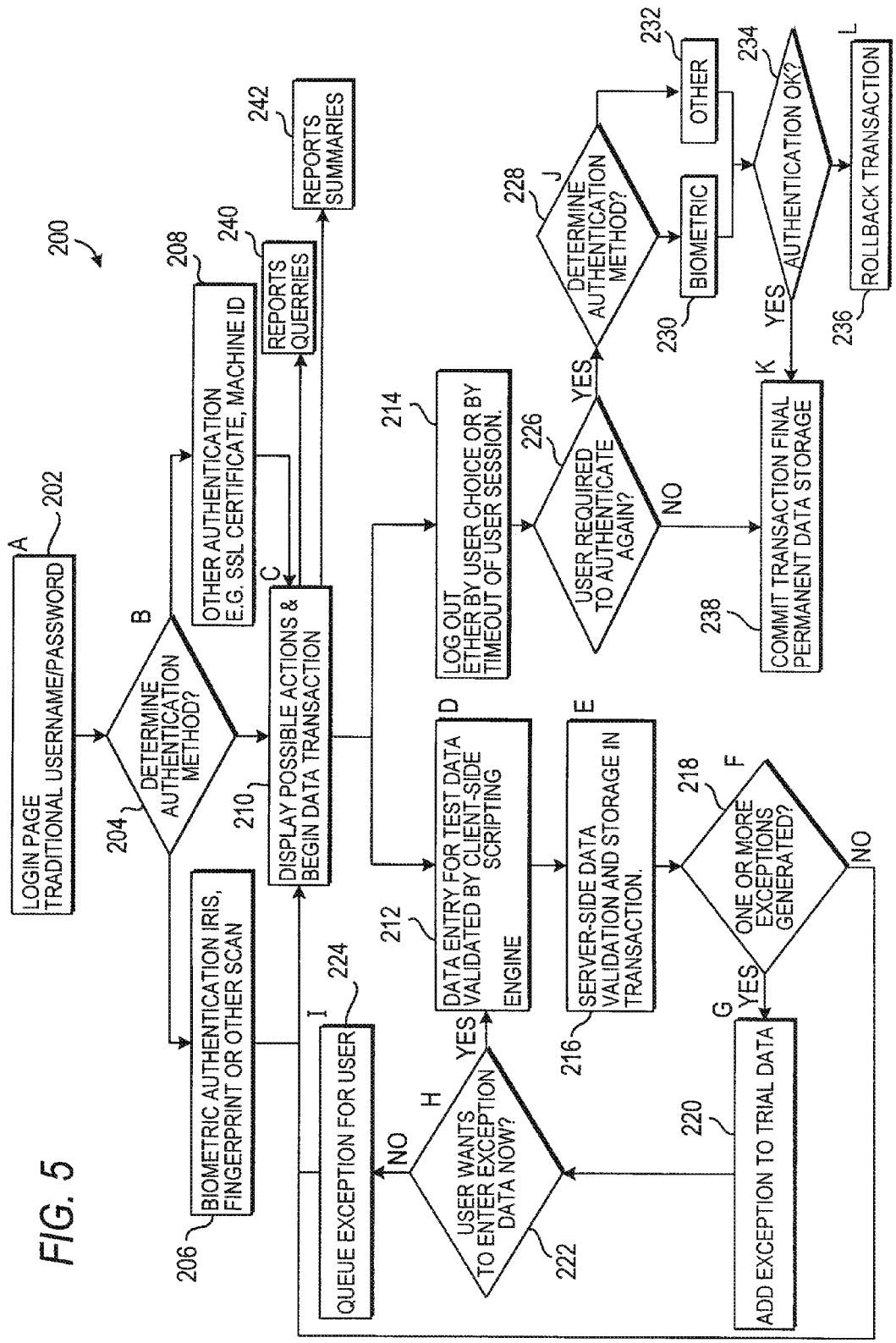
FIG. 5 is a flow diagram of the clinical trial management program of the present invention.

At this point the clinical trial management program of the present invention, shown in FIG. 5, may read in the parameters of the trial established in the application data database 11a (FIG. 1) and automatically generate the appropriate questionnaires and forms to allow the trial participants of the trial to fill in the results of tests 77 (FIG. 4f).

As shown in FIG. 5, the clinical trial management program 200 may be accessed by authorized personnel in step 202 through the login screen 102 (FIG. 4a). In step 204, judging by the login and determining the level of access through the use of the personnel database 11b (FIG. 1), a determination is made of what level of authentication should be performed, or whether authentication is necessary all together. It may be determined that further or additional authentication is required, such as biometrics authentication of a single or multiple trial participants, e.g., in situations where the authentication is used to guarantee the physical interaction between a trial investigator and a trial participant. In such a case authentication steps such as biometrics, e.g., iris or finger print scan, facial recognition, voice print, retinal scan, facial recognition, etc., and/or DNA authentication, e.g., the blood, urine, hair, saliva, tissue sampling, etc., in step 206 or other, e.g., entering social security number, special ID codes, in step 208 may be required before proceeding. Please note that the authentication may be performed on the individual members of the clinical trials, e.g., the trial investigators and the trial participants; or on the plurality of members of the clinical trials concurrently, e.g., a plurality of the trial investigators, a plurality of the trial participants, a combination of the trial investigators and trial participants.

The concurrent authentication of a plurality of members is utilized by the present invention in situations where the authentication is used to guarantee the physical interaction between the trial investigators and the trial participants.

The authentication tests may use flexible timeouts defined by the trial administrator for single and multiple interactive sessions with the trial participant. Moreover, these sessions are location independent. Each computing device 14, 15, 16, and 18 (FIG. 1) used in the authentication may be identified by a unique identification number, therefore the physical location of such components need not be fixed for the authentication purposes.

As described above, the preferred embodiment of the present invention contemplates but is not limited to personnel with predefined purposes. Accommodation of personnel for many diverse purposes, e.g., television, magazine, and newspaper reporters, colleges, hospitals, competitors, statisticians, insurance companies, etc., not described in the preferred embodiment may be easily provided by the inventive system and may be as easily created by these skilled in the art.

By Participants or Investigators

Figure 4D:
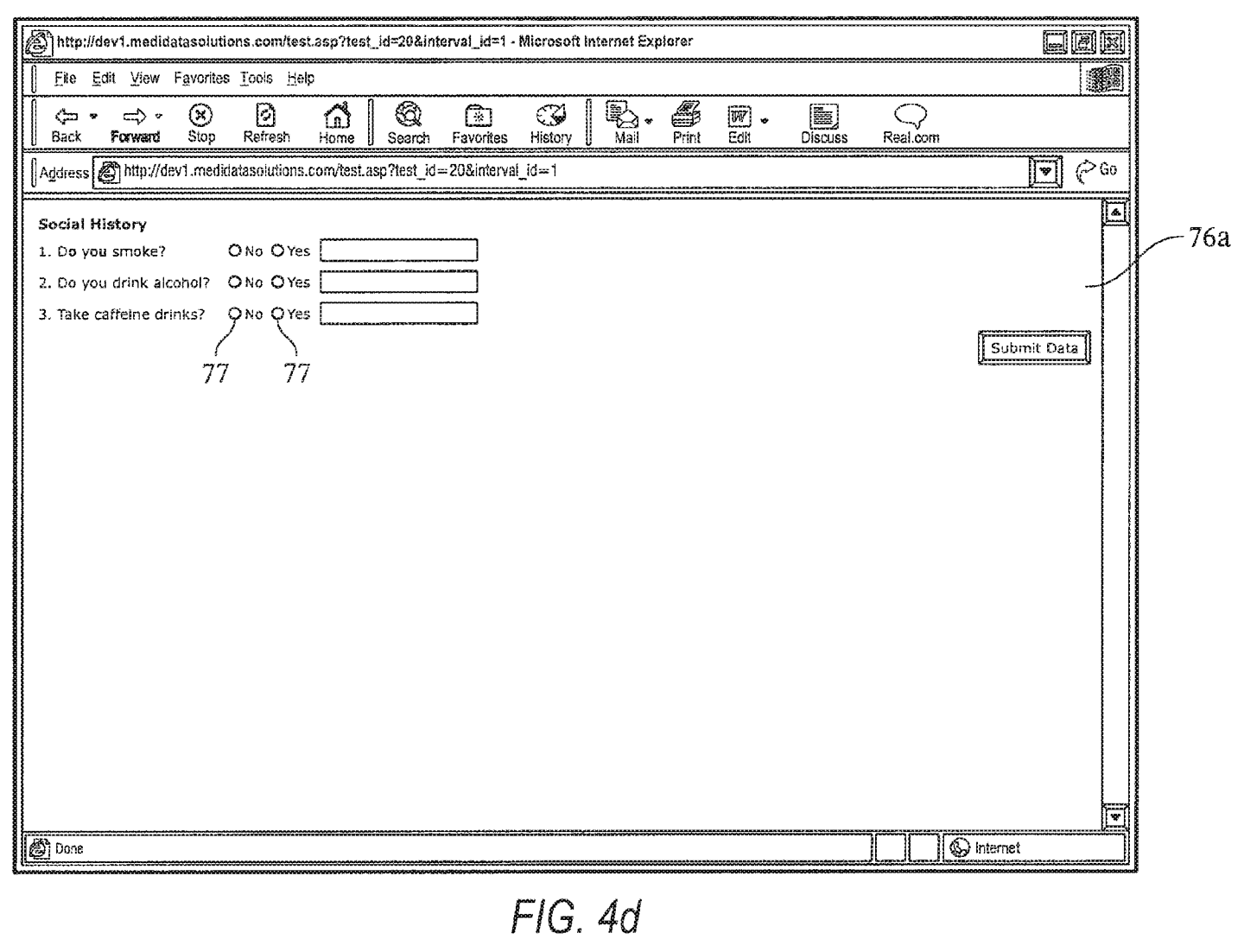

After logging in step 202 and being authenticated in steps 206 or 208, in step 210 the trial investigators and the trial participants will be shown a list of possible tests 72 (FIG. 4c). After selecting a particular entry 76a (FIG. 4c) from the screen 72 (FIG. 4c), the trial investigators and the trial participants are presented with trial data entry screens, e.g., 76a-c (FIGS. 4d-4f).

However, before allowing the entry of the test result data in step 212, the program 200 may determine in step 211 that an informed consent is required before the trial data for the selected test is accepted. The trial investigators or participants are then presented with the informed consent screen or document in step 95. As shown in FIG. 7, the trial investigators and participants will be asked in step 96 to review the consent document along with any necessary supporting documentation. This may be performed by presenting the informed consent document and supplemental information to the patient on the computer screen. A sample Informed Consent Document 300 is shown in FIGS. 8a-8c.

In step 97 the trial investigators and the trial participants will indicate their agreement with the informed consent document either by typing their agreement into a text box on the computer screen or interacting with the clinical trial management program 200 (FIG. 5), for example, by checking a checkbox or clicking a button. In step 98, the trial investigators or the trial participants will then reenter any identifiers entered and saved in the biometric consent database 94 and perform a biometric authentication. The clinical trial management program 200 requires that both the trial investigator's and the trial participant's authentication be performed on the same computing device and within a pre-set period of time, for example, 30 seconds, which insures that the trial investigator and the trial participant have interacted and the consent was given by the trial participant in the presence of the trial investigator. The identifiers and biometric data are compared to the data recorded in the biometric consent database 94 and if they are matched successfully, the successful informed consent agreement is permanently recorded in step 99 in the consent database 94.

Electronic Signature

Figure 9:
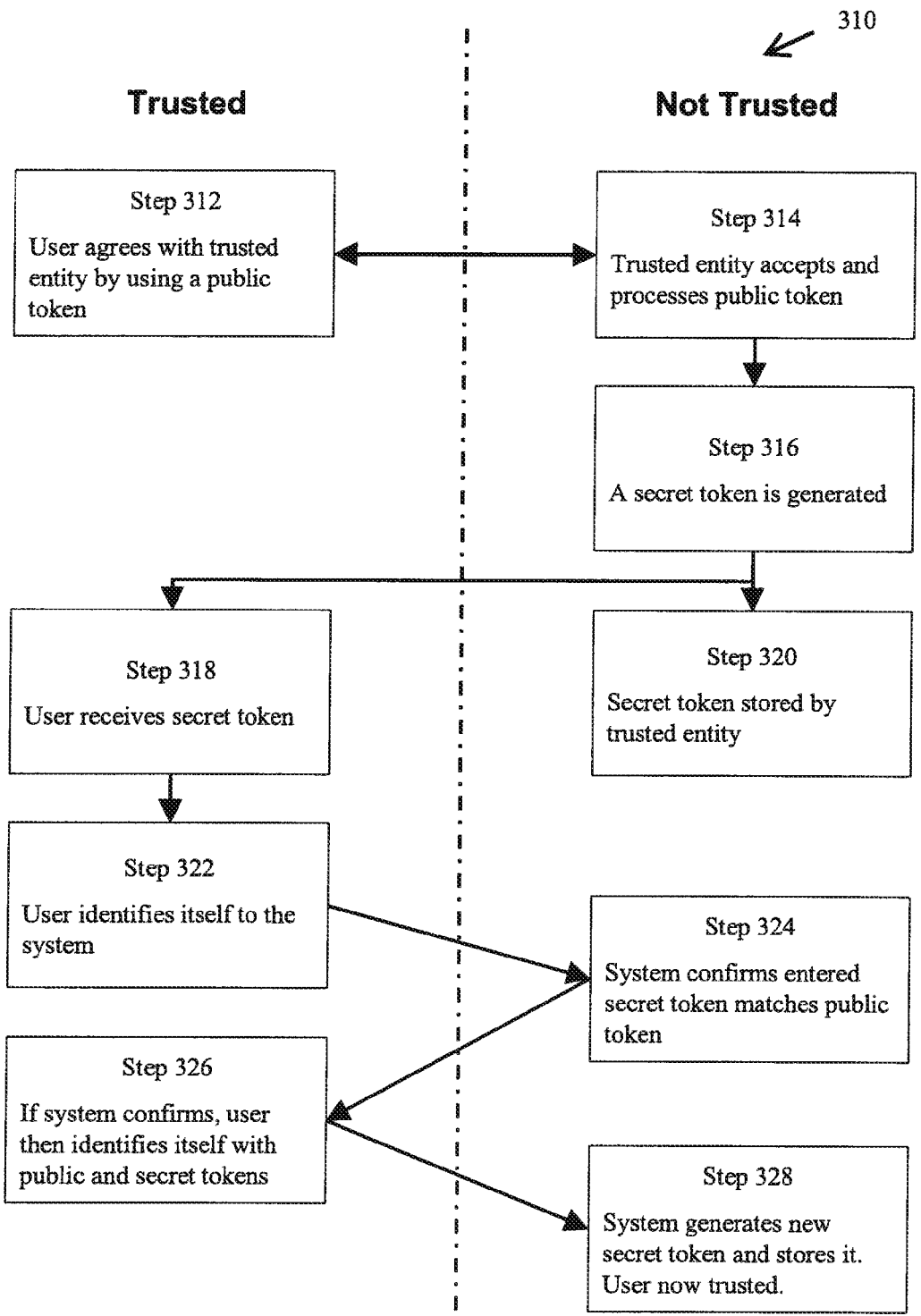
FIG. 9 is a flow diagram for utilizing an electronic signature without the use of the paper signature.

An additional precaution taken by the inventive system in ascertaining the identity of the trial investigators and participants is the use of the electronic signature 302 (FIG. 8c) to verify the consent form 300 electronically. FIG. 9 shows a process 310 for providing means to securely grant access via electronic means of communication, to users who are unknown and initially "not trusted", i.e., any information entered by unknown users can not be used for subsequent analysis by a central organization. Thus, all needs for paper document, e.g., informed consent, transmission, subsequent storage, geographic proximity and/or travel are eliminated.

Traditionally, the first step in assigning an electronic signature for clinical research that will undergo the FDA approval has been a paper-based signature. In that step the user agrees to the following:
1) To use the electronic system appropriately; and
2) To the fact that their electronic signature will be legally binding and a substitute for their physical signature.

The second step is for a member of the authorized organization that is assigning the electronic signature then physically verifies the identity of this person as well.

In step 312 an unknown user performs the requisite first step by agreeing with a trusted entity by using a single public token. The public token is a unique identifying information associated with the users when they interact with the system, i.e., their username. In step 314 the trusted entity accepts and processes the user provided public token. The trusted entity is a human or electronic system that resides within a trusted and closed area defined by an electronic data collection system, such as the present invention. Furthermore, the public token could be a biometric identification, such as a fingerprint or iris scan. A non-biometric public token may be told to or intercepted by any 3$^{rd}$ party at any time without exposing the trusted system to infiltration.

In step 316, a secret token is then generated by the electronic system from the accepted public token. This secret token may be in the form of a simple text token, e.g., a password, or a more complex secret token, such as an encryption key. This secret token is then transmitted, by public means, and is received by the user in step 318. The public means may include a telephone line, e-mail, fax, etc. In step 320, the secret token is stored by the trusted entity along with the user's public token.

Having received the secret token, in step 322, the users electronically identify themselves to the system. Their identification includes their public and secret token and any additional information that the organization may require, for example, the user's full name and contact information could be collected at this time.

In step 324, the system confirms that the entered secret token matches the public token. If it does, a notification is sent to the user by either the same or alternate transmission means confirming that they may access the system. This transmission does not contain any public or secret token information.

Having received the notification, in step 326 the users may be requested once again to electronically identify themselves to the system using their public and secret tokens. After one or more such interactions, in step 328 the system may generate a new secret token or automatically prompt the users to create new secret tokens themselves, e.g., "Please choose a new password." This new secret token is then securely stored in the system and becomes the users second or private token for access. The user is now considered trusted and research data can be collected.

As set forth in FIG. 5, the trial participants start to enter test result data in step 212. The test screens 76a-c (FIGS. 4d-4f) are dynamically generated by the clinical trial management program 200. In step 210 the actions required, i.e., defined in the application data database 11a (FIG. 1), are evaluated and only these required are presented. Furthermore, data entered in response may lead to additional options to be displayed. Actions that have been previously completed are displayed as such, giving instant feedback regarding what was previously entered into the system.

Of course, if after glancing at the list of required actions displayed in step 210 the trial investigator or the trial participant decides not to proceed, in step 214 a logout path may be taken. An in-depth description of the logout procedure will be discussed below.

A transaction of the clinical trial management program 200 begins following the login in step 202 and the authentication in step 204. All the information entered during the session after the login and before the logout is considered a part of this transaction. The transaction will not be committed, i.e., be made a part of the permanent storage 52 (FIG. 2) until the whole session is completed. As data elements 77 (FIGS. 4d-4f) are entered in to the test screens 76a-76c (FIGS. 4d-4f), the clinical trial management program 200 dynamically executes scripts to perform the first level of validation of the data values 77 (FIGS. 4d-4f) entered. The executed scripts may validate entered data values 77 (FIGS. 4d-4f) and may be executed by the browser program, e.g., Microsoft EXPLORER or Netscape NAVIGATOR, using its built-in functionality on the computing devices 14, 15, 16, and 18 (FIG. 1). Moreover, the executed scripts may validate entered data values 77 (FIGS. 4d-4f) on the computing device 12 (FIG. 1) to provide two levels of data validation.

These scripts compare the values 77 (FIGS. 4d-4f) entered, with previously set exception limits 80 (FIG. 3b) defined in the application data database 11a (FIG. 1). In the event where an entered value is outside of these exception limits the inventive clinical trial management program 200 will alert the trial investigator or the trial participant entering the data values 77 (FIGS. 4d-4f) and may request or require additional data to be entered. For example, a confirmation dialog, to insure that the out-of-range value is in fact correct will be interposed in step 216 and the trial investigators and the trial participants may be asked or forced to reply before proceeding.

After all the test values 77 (FIGS. 4d-4f) are completely filled in, step 216 saves these values 77 (FIGS. 4d-4f) in the current transaction, executes the scripts to perform the second level of validation as described above. The values 77 (FIGS. 4d-4f), entered for each element are once again compared with the exception ranges 80 (FIG. 3b) and with the acceptable data change rate. The data change rate is determined by comparing values 77 (FIGS. 4d-4f) to those entered for the same element at previous intervals. Should the values 77 (FIGS. 4d-4f) be either out of the exception range 80 (FIG. 3b) or change at a rate beyond the preset exception change rate for the given element, an exception record 270 (FIG. 6) is added to the current transaction.

In step 218 it is determined if one or more exceptions are generated at the given interval for the given element. If exceptions are generated, in step 219 the trial investigators and participants may be asked to review and sign the consent documents along with any necessary supporting documentation and indicate their agreement with the informed consent document as described above with reference to step 95 (FIG. 7) and described in detail above. After the consent is given in step 95 or if consent is not required as determined in step 219, an exception record causes new tests to be added to the trial participant's complete trial record in step 220 as well as the elements within that new text that must be completed to close the trial participant's participation in the trial. At this point it is possible to offer an option of completing the exception data immediately or to queue the exception for completion at a later time.

If in step 222 it is determined that the exception is to be completed now, the test form for the exception is presented and the data entry loop starting in the step 212 is repeated. Otherwise, in step 224 the exception is queued, and will then appear in the appropriate data entry options of the step 210.

Figure 6B:
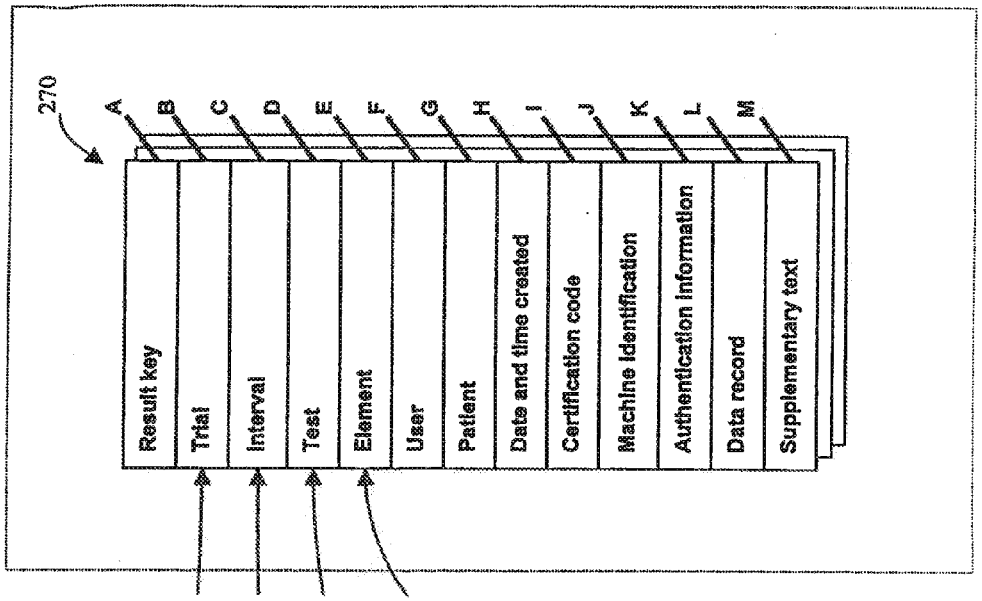
FIG. 6 is a logical relationship design diagram of elements comprising the records of the trial database and their relationship to elements of the application database.
Figure 6A:
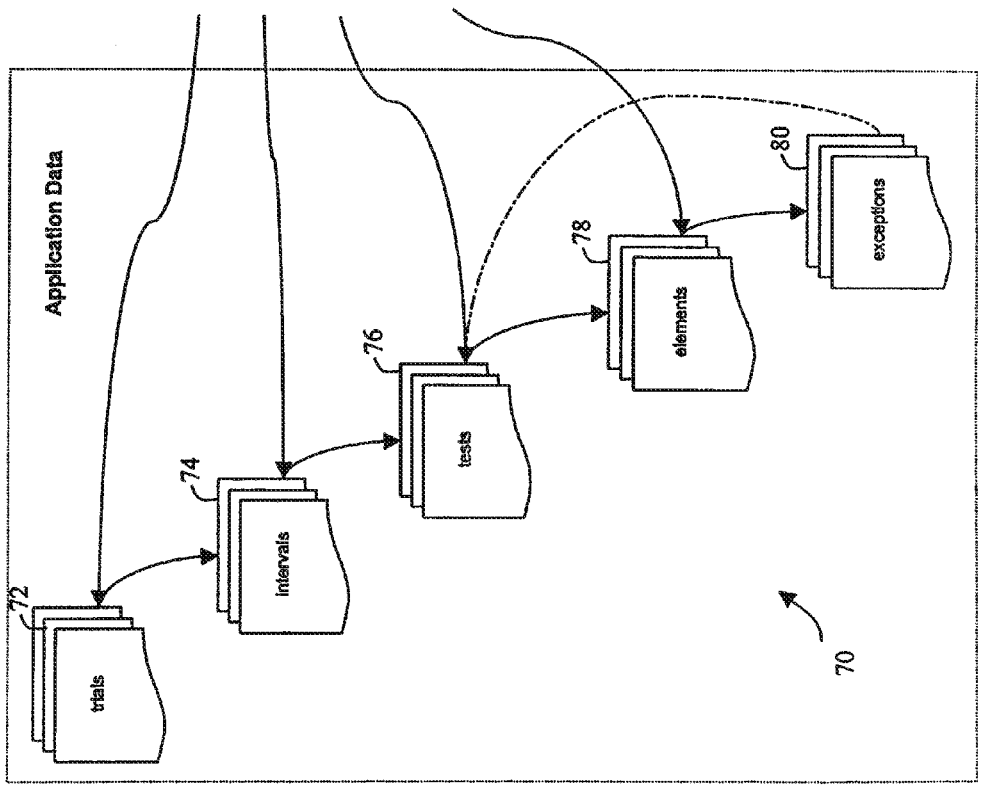

After values 77 (FIGS. 4d-4f) in the transaction are saved, and tests generated from exceptions are completed or queued, the values 77 (FIGS. 4d-4f) may be stored. FIG. 6b shows the record for storing values 77 (FIGS. 4d-4f). Each record 270 comprises the following fields:

1) A unique key 270a used to identify the transaction.
2) A trial key 270b, for pointing to the specific trials table 72 (FIG. 6a) of the application data database 11a (FIG. 1) with which the present record 270 identifies or belongs.
3) An intervals key 270c for identifying the particular interval on the intervals table 74 (FIG. 6a) of the application data database 11a (FIG. 1), which corresponds to the specific value 77 (FIGS. 4d-4f) of the present trial identified by the trial key 270a (FIG. 6).
4) A test key 270d for identifying the particular tests table 76 (FIG. 6a) that the values 77 (FIGS. 4d-4f) are associated with.
5) An element key 270e for identifying or pointing back to the element in the elements table 78 (FIG. 6a) that the values 77 (FIGS. 4d-4f) correspond to.

6) An identification key 270f for identifying the trial personnel who entered the values 77 (FIGS. 4d-4f), such personnel was previously defined in the personnel database 11b (FIG. 1) as described above.

7) A patient identification key 270g associating the values 77 (FIGS. 4d-4f) with the particular trial participant, such trial participant was previously defined in the personnel database 11b (FIG. 1) as described above.

8) A date and time created field 270h for storing the year, month, date, hour, minute, second and millisecond that the values 77 (FIGS. 4d-4f) were recorded.

9) A data certification code field 270i comprising a plurality of random digits.

The current methods of administering a clinical trial involve monitoring the trial centers to assure research integrity. The basic role of the trial monitor is to verify that the data entered by the clinical investigator corresponds to the records taken in the source documentation. The source documentation denotes the trustworthiest record of the data because it contains records of the interactions between the trial investigator and the trial participant and the resultant outcome of any tests taken. The source documentation is held in such high regard because it contains the trial investigator's signature. Usually the source documentation is regarded as the trial participant's medical chart. The present invention describes a method by which the source documentation can be generated by the computer application. All new data values entered into the trial database are grouped according to the date, time, trial participant, computer address, and login episode. For each and every unit of data entered into the trial database 11c (FIG. 1), a multi-digit unique identification number is generated at random. After each log in episode, the trial investigator's computing device 16 (FIG. 1) may print a record of the activities of each patient handled by the trial investigator during any given login episode. This record will act as a legal record of the investigator's actions during a log in episode and be clearly marked with a statement affirming that the investigator has read the record and agrees with it. The investigator will then be asked to sign the record. The signed record can then be utilized as the source documentation since it contains a record of patient data with a verifying signature. The document may be appropriately formatted for placement into the trial participant's chart.

Moreover, the inventive method makes the job of the trial monitor considerably easier. Prior to auditing a site where the trial tests are performed, the trial monitor may print out a list of data transactions and corresponding identification numbers. The trial monitor may then make certain that the events documented in the trial investigator's source documentation contains the correct identification numbers.

Since both the investigator source documentation and monitor transaction list are generated from the same server-side database, there is virtually no possibility for fraud or forgery in this. The trial investigator that tries to change the data values or other parameters entered into the database will create a discrepancy between the source documentation and the data transaction list output for the monitor.

10) A unique identifier field 270j for the identity of the hardware such as the IP address of a network 20 (FIG. 1) connection 60 (FIG. 2) of the computing devices 12, 14, 15, 16, and 18 (FIG. 1).

11) An authentication stamp field 270k generated by the authentication method in steps 206 and 208 (FIG. 5) for the session in progress.

12) An actual data record 270l of the 77 (FIGS. 4d-4f) with data of various types, e.g., text, integer, binary, real, floating, date/time, images, biometrics, etc., keeping their appropriate data type.

13) Any supplemental data 270m entered along with the values 77 (FIGS. 4d-4f) as defined by the element corresponding to the values 77 (FIGS. 4d-4f), for example, an 'other' field in a multiple-choice question.

As shown in FIG. 5, in step 216 each record 270 is recorded in the transaction that covers the entire session from login in step 202 to logout in step 214. In step 226 it is determined from the personnel database 11b (FIG. 1) or from the application data database 11a (FIG. 1) that a logout authentication is required. If authentication is required, in step 228 it is determined which authentication is to be performed, the biometrics, e.g., iris or fingerprint scan, retinal scan, facial recognition, DNA imprinting using hair, saliva, etc., in step 230 or other, e.g., entering social security number, special ID codes, in step 232 may be required before committing the transaction. The authentication may be performed on the individual members of the clinical trials, e.g., the trial investigators and the trial participants or on the plurality of members of the clinical trials concurrently, e.g., a plurality of the trial investigators, a plurality of the trial participants, a combination of the trial investigators and trial participants.

In step 234 it is determined if the required authentication at the end of the session was properly performed or failed. If the authentication failed, in step 236 the transaction is rolled back and the data does not become a permanent part of the trial data. In the alternative the transaction may become a permanent part of the trial data with a recorded indication that the logout authentication failed, or permanently logged outside of the trial data, however the transaction will be rolled back and the data will not become a part of the trial data in the trial data database 11c (FIG. 1). In step 238, the transaction is committed, i.e., recorded as a permanent record in the trial data database 11c (FIG. 1).

Additional determinations may indicate whether transaction comprising the values 77 (FIGS. 4d-4f) will be rolled back in step 236 or committed in step 238. A session may end because the timeout period specified for a particular or a group of the trial participants and trial investigators stored in the personnel database 11b (FIG. 1) has been exceeded.

By Laboratories

A particularly useful feature of the present invention is its ability to accept results for individual trial participants as well as bulk results for groups of trial participants from laboratories connected by computing devices 18 (FIG. 1) to the computing devices 12 (FIG. 1) via the network 20 (FIG. 1) or by a direct digital interface between the laboratory computing devices 18 (FIG. 1) and the computing device 12 (FIG. 1). Where a plurality of samples of the trial participant's specimens, e.g., blood, saliva, or urine, are tested by a particular laboratory, the results may be securely transferred to the trial data database 11c (FIG. 1). The trial participants' privacy may be maintained by providing the laboratories only with the assigned trial participant unique number. The laboratory computing device 18 (FIG. 1) may then cross-reference the trial database 11c (FIG. 1) using the trial participant unique number and input the appropriate laboratory test result. This will eliminate the need for human intervention in inputting the test results and therefore the possibility for human-error or fraud By Monitors As described above, the trial monitor is the entity, person, or persons that constantly monitor the integrity of the trial insofar as the data entered and the conduct of the trial investigators and the trial personnel is concerned. The trial administrator often contracts the trial monitors as part of the CROs or as independent consultants. Typically the trial monitor maintains a record of the activities of the trial investigators and makes certain that the data submitted by the trial investigator corresponds to the source documentation, i.e., the patient's medical record. The trial monitor verifies whether the trial investigator has provided the proper informed consent and that the trial participant's characteristics conform to the inclusion and exclusion criteria specified in the trial protocol. All consents can be compared with all the exceptions (daily, weekly, monthly, per trial) to assure that all the consents were accepted when required. Trial monitors will perform declared and undeclared visits to the trial investigator sites to audit the operations of the trial investigator in-person.

Figure 4G:
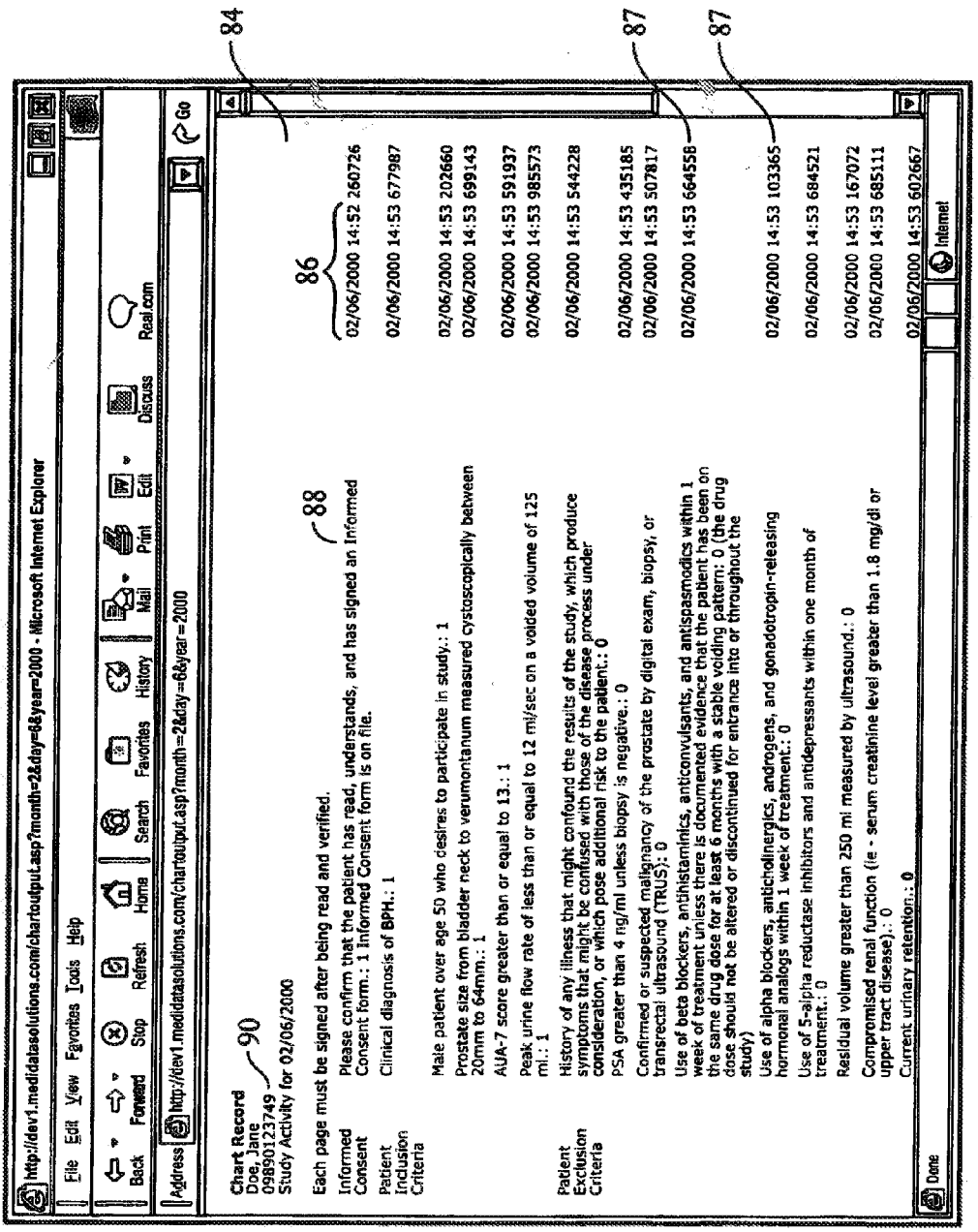
FIG. 4g is a sample report screen of the clinical trial management program listing for the trial monitor various information indicating test performance status.

The inventive system may provide the trial monitor with access to limited information in the trial data database 11c (FIG. 1). While the trial monitors may be free to view all trial participant information from the personnel database 11b (FIG. 1), they may not be able to identify these trial participants except by a unique code assigned to each trial participant for purposes of the trial. Upon entering the inventive system in step 202, the trial monitor may be asked to authenticate himself or herself in steps 206 or 208. This authentication is accomplished using either a form of biometrics measurement in step 206 or by username and password method in step 208. Once the trial monitor is properly logged into the application running on the computing device 12 (FIG. 1), they will have access to the entries of the trial participant related data stored in the personnel databases 11b (FIG. 1) and in the trial data database 11c (FIG. 1) referenced according to specific trial investigators. In step 240, the trial monitors will be able to get complete reports of transactions performed by individual trial investigators, e.g., 84 (FIG. 4g), identified by data stamps including the following:

1) date and time of patient visit 86 (FIG. 4g);
2) interaction and data entry 88 (FIG. 4g);
3) Internet protocol address from which data was entered (not shown);
4) trial investigator identification 90 (FIG. 4g); and
5) a unique encryption stamp for each transaction 87 (FIG. 4g).

These reports may be created for each trial participant according to each time point, of the intervals 74 (FIG. 3b), tracked as per the trial protocol. Furthermore, these reports may enable the trial monitor to verify the trial investigator's source documentation against the data shown in the report. Separate reports may be generated for data that is missing, entered late, changed by the trial investigator, or is out of range.

This may allow the trial monitor to address each specific issue with the trial investigator and to reconcile the problem in the trial data. Separate reports may further be generated for every adverse event reported by the trial investigator. Each report may list the adverse event and the follow-up necessary to be performed by the trial investigator in order to document the ultimate consequences to the trial participant.

Summary reports of the trial monitor's verified values 77 (FIGS. 4c-4f) may be generate each time a trial monitor completes a review of either a single test element 78 (FIG. 3b) or group of tests 76 (FIG. 3b). The verified values 77 (FIGS. 4c-4f) will also be associated with identifying stamps such as date, time, trial monitor's biometrics authentication, etc. This report may ultimately be printed for approval by the trial investigator and signature.

By Administrator

The trial administrator may be given special access to certain forms of data while being restricted to others. For example, while the trial administrator may be able to view overall summary data about a trial, they will be unable to access patient-specific information in order to maintain patient privacy.

The application will have special functions available to the trial administrator. In general, the trial administrator will be able to have a real-time "bird's eye view" of the ongoing clinical trial. After logging in step 202, the trial administrator will be asked to authenticate himself or herself as described above with reference to steps 204, 206 and 208. In step 242 the trial administrator will be enabled to obtain summary data of the trial and application-specific tools to allow manipulation of the summary data.

General functions available to the trial administrator could include summary information, analysis tools, and reporting tools. A summary information area allows the trial administrator access to updates on the status of various trial investigator sites. In doing so, the trial administrator is able to see the performance of each trial investigator via parameters such as the number of patients enrolled or the number of completed patients or the number of delinquencies or the number of adverse events or by the answers to satisfaction-questionnaires about the trial investigators rated by patients/trial participants.

Analysis tools may also be available to the trial administrator such that raw summary data representing the current state of the trial will be able to be manipulated. For example, the trial administrator may be able to apply various statistical analysis functions, i.e., averages, standard deviations, control for data variables, etc., to generate graphs and charts. The trial administrator would also be able to use analysis tools to compare two or more trial investigator sites in terms of performance and view the results in graph or chart format.

Reporting tools may be provided such that the trial administrator can generate reports. For example, a pharmaceutical company testing a new drug may want a report that conforms to the outline of a new drug application; the trial administrator, for academic reasons might want a report that is later submitted as a clinical paper to a medical journal. Templates for various kinds of reports will be available to the trial administrator. The trial administrator will be able to customize their own template, which may consist of a series of headings and hierarchical subheadings to format a document. The reports created may be integrated with the analysis tools such that graphs generated dynamically from the trial data will be incorporated into the report. The application will allow for collaborative authoring and tracking of a document using a system by which parts of a document may be "checked-in" or "checked-out" by multiple trial administrators. The reports created will be able to be output in multiple formats compatible with other word processing software or document readers, i.e., Adobe Acrobat, or Microsoft Word. Ultimately upon completion of the report, the trial administrator may immediately transfer the document electronically to the end viewer such as a peer review committee or a governmental regulatory board.

Reminders

One of the major components of clinical research is the participation of the patients in performing the chore of replying to subjective questionnaires. These questionnaires typically pertain to issues of quality of life, pain scales, and symptom diaries, to name just a few. In addition, subjects involved in clinical research are often asked to take medications that may require strict doses and regimens for route of administration and frequency of consumption.

A major area of deficiency in clinical research is the risk that the patients may forget to take the prescribed medications or answer questionnaires at specified times. This ultimately leads to inaccurate results. Moreover, currently there is no method for instantaneous reporting of events adverse to the patient. Patients are often left to their own initiative to report adverse events that may occur before their next visit to a clinic or a discussion with the trial investigators.

The present invention trains the trial participants to use handheld devices and other electronic data entry clients, such as wireless telephones, to answer questions and to report adverse events. In a fashion described above where the questionnaires are formatted electronically to enable entry of subjective data directly from the trial participants' computing devices 14 (FIG. 1) over the network 20, the same can be accomplished with the use of wireless technologies where the computing device 14 is connected to the network 20 or even to the computing device 12 itself via wireless means.

The present invention enables the trial participants equipped with handheld devices to participate in clinical research. During that research, the trial participants may be prompted at specified times, through their hand held devices, to initiate certain health related activities, such as taking medication. Furthermore, the trial participants may be requested to enter data pertaining to health questionnaires.

Using a predefined list of trial participants, and network addresses of the handheld devices or the telephone numbers if these devices are telephones, the present invention notifies or reminds the trial participants to perform a trial-related activity at a specified time. If appropriate the trial-related activity through the handheld device, e.g., filling out an informed consent and signing it using the electronic signature as described above. Questionnaire data may be entered in to the handheld device via a keyboard, by writing on a screen with a stylus, using interactive voice response (IVR) or a voice recognition systems.

Simultaneously, messages are routed to the trial adminisrtator's computing devices 15 (FIG. 1), which can also be physically or wirelessly connected to the network 20 or an associated health care provider. For example, if the trial participant is unable to be reached, a message, which can be a beep, a voice message, an e-mail, etc., is sent to notify the trial administrator or the associated health care provider to initiate a search for the trial participant. The trial administrator or the associated health care provider can contact one or more trial participants' pager by dialing a telephone number of the pager and sending a call back number to the pager and playing a recorded alerting message when the participant calls the call back number. Alternatively, the trial participant can immediately report any fonn of adverse event in which case the trial adihinistrator or the associated health care provider will also be notified. This feature of the inventive system adds to improved patient safety during the research process of the trial.

While the invention has been particularly shown and described with respect to illustrative and preferred embodiments thereof, it will be understood by those skilled in the art that the foregoing and other changes in form and details may be made therein without departing from the spirit and scope of the invention that should be limited only by the scope of the appended claims.

We claim:

1. A computer based method for authenticating an ongoing clinical trial is conducted in accordance with procedural guidelines, comprising the steps of:

conducting said ongoing electronic clinical trial comprising a plurality of tests according to procedural guidelines established by a clinical trial administrator over a communications network;

selecting a test from said plurality of tests of said ongoing electronic clinical trial to be performed by said trial participant using a computing device connected to said communications network and associated with said trial participant;

providing said informed consent if it is determined that said selected test of said ongoing electronic clinical trial requires a consent, wherein said informed consent signifies that said trial participant understands aspects of said selected test of said ongoing electronic clinical trial and agrees to participate in performance of said selected test of said ongoing electronic clinical trial;

performing said selected test of said ongoing electronic clinical trial by said trial participant to provide trial data if said informed consent is not required or if said informed consent is required and provided by said trial participant;

accepting and recording said trial data of said trial participant in a database connected to said communications network, thereby providing an authentication that trial data recorded in said database occurred in accordance with said procedural guidelines;

scheduling one or more periods for accepting said trial data;

scheduling said plurality of tests to be performed during said one or more periods;

defining a plurality of elements for each of said plurality of tests;

identifying a plurality of exceptions for setting limits on said trial data;

alerting said trial participant to perform a scheduled test; and continuously attempting to reach said trial participant if said trial participant fails to reply.

2. The computer based method of claim 1, further comprising the step of pre-establishing procedural guidelines for conducting said ongoing clinical trial by said clinical trial administrator, said procedural guidelines identifying which of said plurality of tests require said informed consent from said trial participant.

3. The computer based method of claim 2, further comprising the steps of:

detecting any discrepancy in said trial data; and requesting said trial participant to provide said informed consent if a discrepancy is detected in said trial data.

4. The computer based method of claim 3, further comprising the step of prohibiting said trial participant from participating in said ongoing electronic clinical trial if said informed consent was not received from said trial participant.

5. The computer based method of claim 1, further comprising the step of prohibiting said trial participant from performing said selected test if it is determined that said informed consent is required and not provided by said trial participant.

6. The computer based method of claim 1, wherein the step of alerting further comprises the step of sending an alert message to a network address of said computing device associated with said trial participant.

7. The computer based method of claim 1, Wherein the step of alerting further comprises the steps of calling a telephone associated with said trial participant and playing a recorded alert message when said trial participant answers said telephone; or calling a pager associated with said trial participant, sending a call back number to said pager and playing a recorded alert message when said trial participant calls said call back number.

8. A computer based method for authenticating that a clinical trial electronically conducted over a communications network is conducted in accordance with procedural guidelines, said clinical trial having a plurality of members comprising at least one trial administrator, at least one trial monitor, at least one trial investigator, and a plurality of trial participants, each member being associated with a computing device connected to said communications network for performing a plurality of transactions of said clinical trial, the method comprising the steps of:

establishing procedural guidelines for said clinical trial by said at least one trial administrator;

conducting said clinical trial using said computing device associated with said trial participant by having said trial participant perform a plurality of tests to provide trial data in accordance with said procedural guidelines;

determining if there is a discrepancy in said trial data received from said computing device associated with said trial participant while said clinical trial is ongoing;

accepting and requesting an informed consent if said discrepancy is found in said trial data;

recording said trial data of said trial participant in a database connected to said communications network if it is determined that there is no discrepancy in said trial data or if said informed consent is received by said trial participant if said discrepancy is found, thereby providing an authentication that trial data recorded in said database occurred in accordance with said procedural guidelines;

scheduling one or more periods for accepting said trial data;

scheduling said plurality of tests to be performed during said one or more periods;

defining a plurality of elements for each of said plurality of tests;

identifying a plurality of exceptions for setting limits on said trial data;

alerting said trial participant to perform a scheduled test; and continuously attempting to reach said trial participant if said trial participant fails to reply.

9. The computer based method of claim 8, further comprising the steps of:

selecting said at least one trial monitor and said at least one trial investigator by said at least one trial administrator;

selecting said trial participant to be enrolled in said clinical trial by said at least one trial investigator; and monitoring said clinical trial by said at lest one trial monitor to detect any deviations from said procedural guidelines.

10. The computer based method of claim 8, further comprising the steps of authenticating said trial participant and accepting said trial data only if said trial participant has been authenticated.

11. The computer based method of claim 9, wherein the step of selecting said at least one trial investigator comprises the step of selecting said at least one trial investigator through an open enrollment and anyone qualified to act as a trial investigator is permitted to register as said at least one trial investigator.

12. The computer based method of claim 9, wherein the step of selecting said at least one trial investigator comprises the step of selecting said at least one trial investigator by an invitation-only enrollment kind said at least one trial administrator registers said at least one trial investigator.

13. The computer based method of claim 8, further comprising the steps of:

receiving identification of said at least one trial administrator and said plurality of trial participants to be enrolled in said clinical trial; and defining a plurality of exceptions for setting limits on said trial data.

14. The computer based method of claim 8, further comprising the step of permitting access to said trial data by a member based on an assigned access level of said member.

15. The computer based method of claim 13, further comprising the step of permitting access to said trial data by said at least one trial investigator based on identification of said trial participant.

16. The computer based method of claim 13, further comprising the step of permitting access to said trial data by said at least one trial monitor based on identification of said trial participant.

17. The computer based method of claim 13, further comprising the steps of authenticating a member and prohibiting said member from performing a transaction if said member is not authenticated.

18. The computer based method of claim 8, further comprising the steps of:

determining an access level and a level of authentication to perform a transaction;

authenticating a member to determine if said member has said level of authentication to perform said transaction;

performing said transaction by said member if it is determined that said member has said level of authentication; and prohibiting said member from performing said transaction if is determined that said member does not have said level of authentication.

19. The computer based method of claim 18, wherein said transaction involves accessing said trial data; and further comprising the steps of:

authenticating said member to determine if said member has said access level to perform said transaction;

performing said transaction by said member if it is determined that said member has said access level; and prohibiting said member from performing said transaction if is determined that said member does not have said access level.

20. The computer based method of claim 17, wherein the step of authenticating utilizes a biometrics method to authenticate said member.

21. The computer based method of claim 20, further comprising the step of performing said transaction if said member is authenticated and storing said transaction and results of said transaction in said database.

22. The computer based method of claim 20, further comprising the step of storing said transaction as a failed transaction in said database if said member is not authenticated.

23. The computer based method of claim 21, further comprising the step of establishing a time limit for performing said transaction by said member if said is authenticated.

24. The computer based method of claim 23, wherein said time limit is established by said at least one trial administrator; and further comprising the step of prohibiting said member from performing said transaction if said time limit has expired.

25. The computer based method of claim 17, wherein said transaction involves performing said plurality of tests; and further comprising the steps of displaying said plurality of tests and said plurality of elements of said plurality of said tests to said trial participant on said computing device associated with said trial participant if said trial participant is authenticated; accepting said trial data from said computing device associated with trial participant if said trial data conforms to said plurality of elements; and determining if said trial data is outside said limits.

26. The computer based method of claim 25, further comprising the steps of dynamically generating said plurality of elements for said one or more periods and displaying only those elements that require said trial data from said trial participant on said computing device associated with said trial participant.

27. The computer based method of claim 26, further comprising steps of receiving a corrected trial data or a confirmation that said trial data is correct if it is determined that said trial data is outside said limits.

28. The computer based method of claim 27, further comprising the step of receiving said trial data comprising at least one of the following values:
- a unique key for identifying said transaction;
- a trial key for identifying said clinical trial;
- a key for identifying a first test in said plurality of tests of said clinical trial identified by said trial key;
- an intervals key for identifying each of said one or more periods for performing said first test;
- an element key for identifying each of said plurality of elements;
- an identification key for identifying said at least one trial investigator and said trial participant providing said trial data;
- a patient identification key for identifying said trial participant;
- a date and time value for storing temporal values of recording of said trial data;
- a data certification code comprising a plurality of random digits;
- a unique identifier to identity said computing device associated with said trial participant; and
- an authentication value for identifying an authentication method used for authenticating said trial participant.

29. The computer based method of claim 28, further comprising the step of generating a plurality of reports of said plurality of transactions from said trial data retrieved from said database according to at least one of the following criteria:
- a date and time of each of said plurality of transactions;
- a network address of said computing device from which said trial data was entered by said trial participant;
- an identification of said at least one trial investigator;
- an identification of the computing device on which said transaction was entered by said member; and
- a unique encryption stamp associated wit said transaction.

30. The computer based method of claim 29, further comprising the step of finding said discrepancy based on plurality of reports to verify veracity of said clinical trial.

31. The computer based method of claim 30, further comprising the step of evaluating the performance of said at least one trial investigator based on said plurality of reports.

32. The computer based method of claim 31, further comprising the step of electronically conducting said clinical trial over the Internet.

* * * * *

UNITED STATES PATENT AND TRADEMARK OFFICE
CERTIFICATE OF CORRECTION

PATENT NO. : 7,596,541 B2
APPLICATION NO. : 10/416380
DATED : September 29, 2009
INVENTOR(S) : deVries et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 861 days.

Signed and Sealed this

Twenty-eighth Day of September, 2010

David J. Kappos
*Director of the United States Patent and Trademark Office*